United States Patent [19]

Adams, Jr.

[11] Patent Number: 4,534,788

[45] Date of Patent: Aug. 13, 1985

[54] HERBICIDAL SULFONAMIDES

[75] Inventor: John B. Adams, Jr., Hockessin, Del.

[73] Assignee: E. I. Du Pont de Nemours and Company, Wilmington, Del.

[21] Appl. No.: 538,261

[22] Filed: Nov. 15, 1983

Related U.S. Application Data

[60] Division of Ser. No. 152,021, May 30, 1980, Pat. No. 4,452,628, which is a continuation-in-part of Ser. No. 60,869, Jul. 26, 1979, abandoned.

[51] Int. Cl.$^3$ .................. A01N 47/36; C07D 239/42

[52] U.S. Cl. .......................... 71/92; 544/321; 544/332

[58] Field of Search .................. 544/321, 332; 71/92

[56] References Cited

U.S. PATENT DOCUMENTS 4,394,506  7/1983  Levitt ................................. 544/321

Primary Examiner—Robert Gerstl

[57] ABSTRACT

This invention pertains to benzenesulfonamides and their use as agricultural chemicals.

24 Claims, No Drawings

HERBICIDAL SULFONAMIDES

RELATED APPLICATIONS

This application is a divisional application of my copending application U.S. Ser. No. 152,021 filed May 30, 1980, U.S. Pat. No. 4,452,628, which is a continuation in part of my application U.S. Ser. No. 060,869, filed July 26, 1979, now abandoned.

BACKGROUND OF THE INVENTION

This invention relates to benzenesulfonamides which are useful as agricultural chemicals.

French Pat. No. 1,468,747 discloses the following para-substituted phenylsulfonamides, useful as antidiabetic agents:

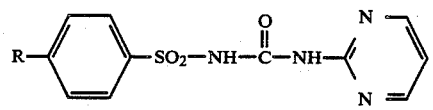

where R=H, halogen, $CF_3$ or alkyl.

Logemann et al., Chem. Abstr., 53, 18052 g (1959), disclose a number of sulfonamides, including uracil derivatives and those having the formula:

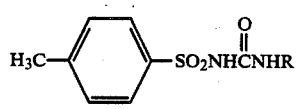

wherein R is butyl, phenyl or

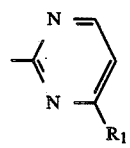

and $R_1$ is hydrogen or methyl. When tested for hypoglycemic effect in rats (oral doses of 25 mg/100 L g), the compounds in which R is butyl or phenyl were most potent. The others were of low potency or inactive.

Wojciechowski, J. Acta. Polon. Pharm. 19, p. 121-5 (1962) [Chem. Abstr., 59, 1633e] describes the synthesis of N-[(2,6-dimethoxypyrimidin-4-yl)aminocarbonyl-4-methylbenzenesulfonamide:

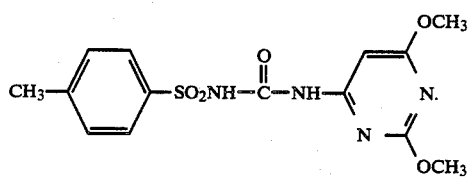

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides:

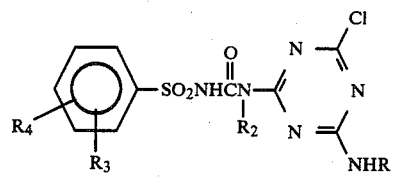

wherein $R_1$ and $R_2$ may independently be alkyl of 1-4 carbon atoms; and $R_3$ and $R_4$ may independently be hydrogen, chlorine or alkyl of 1-4 carbon atoms.

Compounds of Formula (ii), and their use as antidiabetic agents, are reported in J. Drug. Res. 6, 123 (1974):

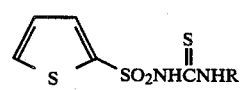

wherein R is pyridyl.

The presence of undesired vegetation causes substantial damage to useful crops, especially agricultural products that satisfy man's basic food needs, such as soybeans, wheat and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

According to this invention, there is provided compounds of Formula (I) and their agriculturally suitable salts, suitable agricultural compositions containing them, and methods of using them as selective, as well as general herbicides having both pre-emergence and post-emergence activity. These compounds are highly active herbicides. They are especially useful for controlling weeds in wheat.

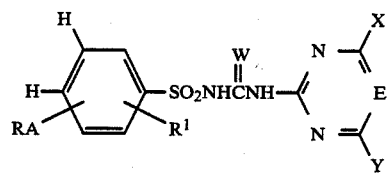

wherein
W is O or S;
R is $CHF_2$, $CF_3$, $CH_2CF_3$ or $CF_2CHFG$, where G is F, Cl, $CF_3$ or Br;
A is O or $S(O)_n$, where n is 0, 1 or 2;
$R^1$ is H, F, Cl, Br or $CH_3$;
X is $CH_3$ or $OCH_3$;

Y is $CH_3$, $OCH_3$, $OCH_2CH_3$, $(CH_2)_mOCH_3$ (where m is 1 or 2), $OCH_2CH_2OCH_3$, or $OCHR^2CO_2R^3$, where $R^2$ is H or $CH_3$ and $R^3$ is $CH_3$ or $C_2H_5$; and E is CH or N.

Preferred in order of increasing preference for reasons of increased activity or ease of synthesis, or both, are:

(1) Compounds of Formula (I), wherein W is O.
(2) Compounds of preference (1), wherein Y is $CH_3$ or $CH_3O$.
(3) Compounds of preference (2), wherein A is O, S or $SO_2$.
(4) Compounds of preference (2), wherein $R^1$ is H or Cl.
(5) Compounds of preference (3), wherein $R^1$ is H or Cl.

Specifically preferred for their outstanding biological activity or very favorable ease of synthesis, or both, are:

5-chloro-N-[(4,6-dimethylpyrimidin-2-yl)aminocarbonyl]-2-(trifluoromethoxy)benzenesulfonamide;
2-chloro-N-[(4,6-dimethylpyrimidin-2-yl)aminocarbonyl]-5-(trifluoromethoxy)benzenesulfonamide;
N-[(4,6-dimethylpyrimidin-2-yl)aminocarbonyl]-2-(1,1,2,2-tetrafluoroethoxy)benzenesulfonamide;
N-[(4-methoxy-6-methyl-1,3,5-triazin-2-yl)aminocarbonyl]-2-(1,1,2,2-tetrafluoroethoxy)benzenesulfonamide;
N-[(4,6-dimethoxypyrimidin-2-yl)aminocarbonyl]-2-(1,1,2,2-tetrafluoroethoxy)benzenesulfonamide; and
N-[(4-methoxy-6-methylpyrimidin-2-yl)aminocarbonyl]-2-(1,1,2,2-tetrafluoroethoxy)benzenesulfonamide, alone or in admixture.

DETAILED DESCRIPTION

Synthesis

Since not all of the compounds included within Formula (I) can be made by the same synthesis scheme, Formula (I) is divided into compound groups II and III, synthesis for each of which is discussed separately; compound groups II and III are:

(Haloalkoxy)benzenesulfonylureas

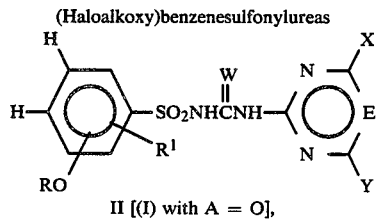

II [(I) with A = O], and (Haloalkylthio, haloalkylsulfinyl, and haloalkylsulfonyl)benzenesulfonylureas

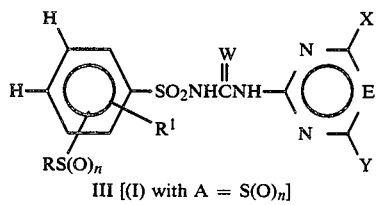

III [(I) with A = $S(O)_n$]

(Haloalkoxy)benzenesulfonylureas

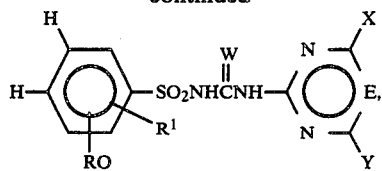

wherein the substituents are defined as for Formula (I).

(Haloalkoxy)benzene derivatives (1) as starting materials for preparation of II can be made by methods well known in the art.

(Trifluoromethoxy)benzene derivatives can be made by the method of Sheppard [J. Org. Chem. 29, 1 (1964)], e.g.:

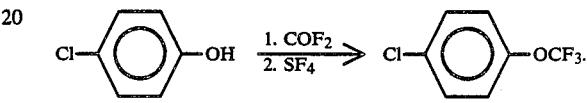

(Tetrahaloethoxy)benzene derivatives can be made by the method of England et al. [J. Am. Chem. Soc. 82, 5116 (1960)], which also applies to the hexafluoropropoxy compounds, e.g.

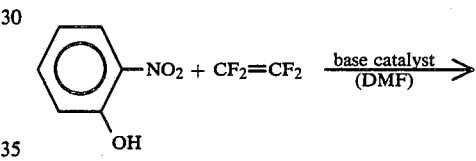

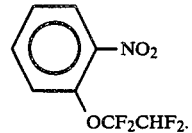

The latter compound can be purchased from Fairfield Chemical Co., Blythewood, S.C.

(Trifluoroethoxy)benzene derivatives can be made by reaction of trifluoroethanol with an activated aromatic halide, e.g.:

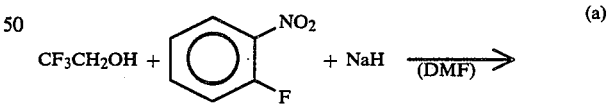
(a)

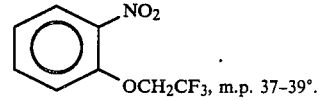
m.p. 37–39°.

In reaction (a) sodium hydride and trifluoroethanol are mixed in an aprotic solvent, such as dimethylformamide (DMF), dioxane or tetrahydrofuran (THF), with 2-(fluoro or chloro)-1-nitrobenzene. The reaction proceeds to completion at ambient temperature. Heat may be applied (e.g., with a steam bath) if desired to speed the reaction to completion. The product is isolated by diluting the reaction mixture with water, extracting with an organic water-immiscible solvent and evaporation of the solvent. This reaction is similar to that described in Japanese Pat. No. 5 2057-320.

(Difluoromethoxy)benzene derivatives can be made by the method of Yagupol kii et al. [Chem. Abstr. 70, 96318d (1969)]e.g.:

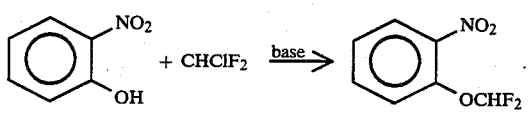

Preparation of compound II is shown schematically, first for the case wherein R is CF₃ or CF₃CH₂:

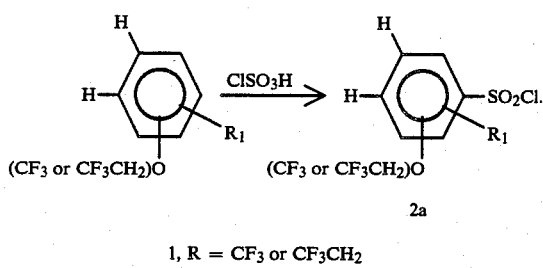

1, R = CF₃ or CF₃CH₂

Chlorosulfonation of aromatic substrates is well known (e.g., L. F. Fieser and M. Fieser, "Advanced Organic Chemistry", 696–698, Reinhold, N.Y., 1961). The chlorosulfonation can be accomplished by addition of the trifluoromethoxy compound to the chlorosulfonic acid or vice versa, optionally in the presence of a cosolvent, such as an alkane or chlorinated alkane (e.g., hexane, 1-chlorobutane, methylene chloride, etc.). The reaction temperature is not critical, with a range of about −5° to 50° operable and ambient temperature (e.g. 20° to 30°) preferred, for convenience. At ambient temperature some hydrolysis of the trifluoromethoxy group occurs. At lower temperatures, chlorosulfonation occurs more slowly with less of the hydrolysis, while at higher temperatures, chlorosulfonation occurs more rapidly with more accompanying hydrolysis. Reaction time at ambient temperature is about 1 to 24 hours, depending on the exact substrate being chlorosulfonated, with an overnight period (about 16 hours) satisfactory. Chlorosulfonation of the tetrahaloethoxy, hexafluoropropoxy and difluoromethoxy compounds is more difficult to control without hydrolysis of the haloalkoxy group than is chlorosulfonation of the trifluoromethoxy or trifluoroethoxy compounds.

The aromatic sulfonyl chloride is conveniently isolated from the reaction mixture by pouring the mixture into ice water, followed by extraction with a water-immiscible organic solvent in which the aromatic sulfonyl chloride is soluble. Such solvents include 1-chlorobutane, methylene chloride, 1,2-dichloroethane, ethyl acetate, toluene and diethyl ether. The solution of the sulfonyl chloride can be dried and evaporated to provide the sulfonyl chloride, which can be further purified by distillation, preferably in vacuum to suppress any thermally dependent decomposition. Alternatively, the solution of the sulfonyl chloride can be used directly in reaction with ammonia in the next step, preparation of the sulfonamide.

Chlorosulfonation of 1 can produce isomeric mixtures, e.g.:

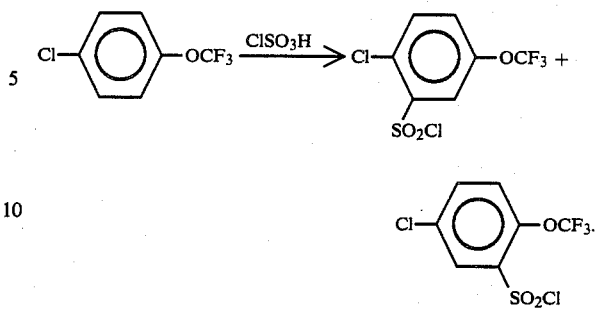

Such isomeric mixtures can be separated by conventional routes (e.g., fractional distillation, chromatography) or used without separation. In the latter case, isomeric mixtures of sulfonamides, sulfonyl isocyanates and thiocyanates, sulfonylureas and sulfonylthioureas are formed in the subsequent reactions. Similarly, the isomeric mixtures of intermediates formed further in the synthesis sequence can be separated or used as isomeric mixtures; isomeric mixtures of product sulfonyl (ureas and thioureas) can be used as herbicides or separated and used as individual compounds.

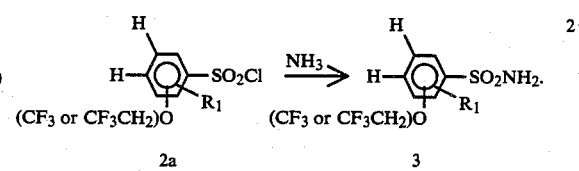

Conversion of sulfonyl chlorides to sulfonamides is well known (e.g., L. Fieser and M. Fieser, op. cit., 699). It is convenient to dissolve the sulfonyl chloride 2a in an inert solvent, e.g. toluene, ethyl acetate, tetrahydrofuran, etc., and sparge in gaseous ammonia until the formation of ammonium chloride (insoluble in the solvent) ceases. Temperature is not critical and can range from about −20° to the boiling point of the solvent. For convenience, ambient temperatures are preferred.

The product can be isolated from the reaction mixture by evaporation and treatment of the residue with water to remove ammonium chloride. If the product precipitates during reaction it can be removed by filtration of the reaction mixture and washing with water. If the product remains in solution in the reaction mixture and the solvent is water-immiscible, the mixture can be washed with water and the product obtained by evaporation of the solvent. If the product remains in solution in the reaction mixture and the solvent is water-miscible, the product can be precipitated by addition of water, then recovered by filtration.

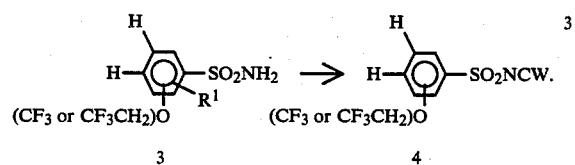

The sulfonamide 3 is converted to the sulfonyl isocyanate or sulfonyl isothiocyanate 4.

Sulfonyl isocyanates can be made by the method of Ulrich et al. [J. Org. Chem. 34, 3200 (1969)]:

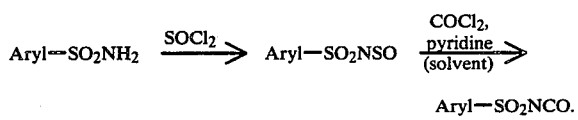

Aryl—SO$_2$NH$_2$ $\xrightarrow{\text{SOCl}_2}$ Aryl—SO$_2$NSO $\xrightarrow[\text{(solvent)}]{\text{COCl}_2,\text{ pyridine}}$ Aryl—SO$_2$NCO.

The sulfonamide is boiled under reflux with an excess of thionyl chloride, which functions as a reactant and solvent. The reaction is continued until the sulfonamide protons are undectable in the proton resonance spectrum. An overnight reaction period (about 16 hours) is generally sufficient. The thionyl chloride is evaporated and the residue dissolved in an inert solvent, such as toluene, benzene, xylene, etc., treated with a catalytic amount of pyridine, then with at least one equivalent of phosgene. The mixture is heated to about 60°–140°, with 80°–100° preferred. Conversion to the isocyanate is substantially complete within about ¼ to 3 hours. The mixture containing the sulfonyl isocyanate can be used directly for the next reaction step (formation of sulfonylurea) or the sulfonyl isocyanate can be isolated in purified form by filtration and evaporation of the filtrate, optionally followed by vacuum distillation.

Sulfonyl isocyanates can also be made by mixing the sulfonamide, an alkyl isocyanate (e.g. butyl isocyanate) and a catalytic amount of 1,4-diaza[2.2.2]-bicyclooctane (DABCO) in xylene or other inert solvent of sufficiently high boiling point (e.g. >135°), heating to about 135°, and adding phosgene until an excess is present (indicated by a drop in boiling point). The mixture is further heated and excess phosgene driven off. After the mixture is cooled and filtered from insoluble material, the solvent, alkyl isocyanate and excess phosgene are evaporated, leaving the crude sulfonyl isocyanate, optionally purified further by vacuum distillation.

Sulfonyl isothiocyanates can be made by the method of Hartke [Chem. Abstr. 64, 15783e (1966)]:

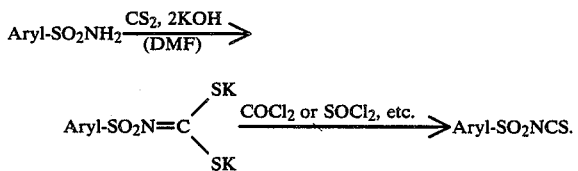

The sulfonamide in dimethylformamide (DMF) is treated with an equivalent of carbon disulfide and 2 equivalents of powdered potassium hydroxide at about 35°. The mixture is stirred (about 1–8 hours) until solution is substantially complete, then diluted with an aprotic solvent, such as ethyl acetate, to precipitate the intermediate dipotassium salt shown. The latter is separated by filtration from the reaction mixture, suspended in an inert solvent, such as toluene, and treated with 2 moles of phosgene (or thionyl chloride, etc.) at about 0°. The mixture is allowed to warm to ambient temperature, filtered, and the sulfonyl isothiocyanate used in solution for the next reaction step (formation of sulfonylthiourea) or isolated by evaporation of solvent. The sulfonyl isothiocyanates may dimerize or trimerize in some cases, but the dimers and trimers still function to provide the sulfonylthioureas in the next reaction step (No. 4).

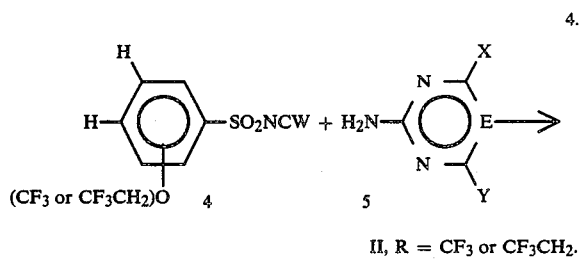

II, R = CF$_3$ or CF$_3$CH$_2$.

The sulfonyl isocyanate or isothiocyanate 4 reacts with the aminoheterocycle 5 to provide the (trifluoromethoxy or trifluoroethoxy)benzenesulfonyl(urea or thiourea) II (with R=CF$_3$ or CF$_3$CH$_2$). This reaction is best carried out in inert organic solvent, such as acetonitrile, tetrahydrofuran, methylene chloride, etc. The reaction is generally exothermic. Conveniently, the starting reaction temperature is ambient, but can be varied from about 0° to 100° if desired. The product can be isolated by filtration if it precipitates from the reaction mixture, otherwise the solvent can be evaporated and the residual product obtained thereby, with optional further purfication obtained by trituration with an organic solvent (e.g., diethyl ether, 1-chlorobutane, etc.) in which it is only sparingly soluble.

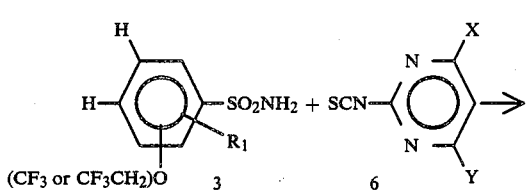

II, W = S, R = CF$_3$ or CF$_3$CH$_2$.

Reaction 5 represents an alternative method for preparation of sulfonylthioureas. The sulfonamide 3 reacts with the heterocyclic isothiocyanate 6 to form the sulfonylthiourea II (with W=S and R=CF$_3$ or CF$_3$CH$_2$). The heterocyclic isothiocyanates 6 used in this procedure can be made, for example, by the method of Japan patent application Pub: Kokai 51-143686, June 5, 1976, or that of W. Abraham and G. Barnikow, Tetrahedron 29, 691 (1973). Reaction 5 is carried out in an inert polar solvent such as acetone or methyl ethyl ketone, at 20° to 50°, in the presence of a basic catalyst such as potassium carbonate or sodium carbonate, in about 1 to 10 hours. The alkali metal salt of the sulfonylthiourea is filtered off, suspended in water, and the pH adjusted down to 1–3 with mineral acid (e.g. hydrochloric acid) to form the product sulfonylthiourea, which is recovered by filtration.

As an alternative to reaction 1, the sulfonyl chloride can be made from the corresponding aniline compound 7 by diazotization, then treatment with sulfur dioxide and cuprous chloride. It should be emphasized that whereas reaction 1, is written as applicable to compounds where R=CF$_3$ or CF$_3$CH$_2$ (i.e., to trifluoromethoxy or trifluoroethoxy compounds), reaction 6 is applicable to compounds where R=CF$_3$, CH$_2$CF$_3$, or tetrahaloethyl, CHF$_2$ or hexafluoropropyl; thus reaction 6 is of more general applicability than reaction 1.

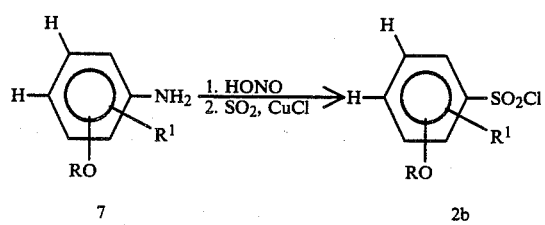

6.

Compound 7, where R is CF$_3$, tetrahaloethyl, HCF$_2$ or hexafluoropropyl can be produced by methods described by Sheppard (loc. cit.), England (loc. cit.) and Yagupol kii (loc. cit.). The aniline compound 7 is diazotized according to methods well known in the art, such as the addition of sodium nitrite to a hydrochloric acid solution of the compound 7. The intermediate diazonium compound is added, as in the well known Sandmeyer-type reaction, to a mixture of cuprous chloride, sulfur dioxide, and acetic acid at reduced temperature, e.g. 0° to 20°. The mixture is kept cold for ¼ to 2 hours, then is allowed to warm to ambient temperature and continue to react until nitrogen evolution has substantially stopped. Dilution with water precipitates the sulfonyl chloride, generally as an oil, which is extracted into a water-immiscible organic solvent, e.g. 1-chlorobutane, diethyl ether, toluene, ethyl acetate and the like. The organic extract can be dried and evaporated to the sulfonyl chloride or the solution can be used directly in the next step (sulfonamide preparation).

The sulfonyl chloride 2b can be used in the same sequential manner as sulfonyl chloride 2a to produce the corresponding sulfonamides, sulfonyl isocyanates and isothiocyanates, sulfonylureas, and sulfonylthioureas.

When a nitration reaction is used to make the precursor to 7, in some cases isomeric mixtures are formed, e.g.:

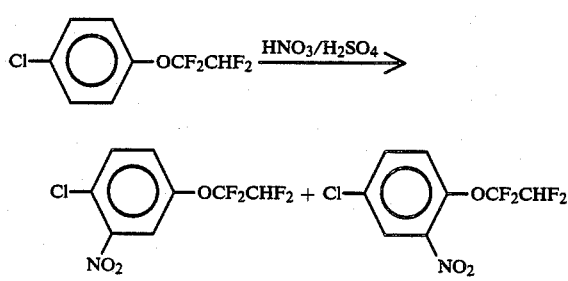

The resulting isomeric mixtures can be separated by conventional means (e.g., fractional distillation or chromatography), or used as such; in the latter case isomeric mixtures of the aniline 7, sulfonyl chloride, sulfonamide, sulfonyl isocyanate and isothiocyanate, sulfonylurea and sulfonylthiourea are found in the reactions which follow. Likewise, the isomeric mixtures of intermediates further in the synthesis sequence can be separated or used as the isomeric mixtures; and isomeric mixtures of product sulfonyl(ureas and thioureas) can be used as herbicides or separated and so used.

(Haloalkylthio, haloalkylsulfinyl and haloalkyl(sulfonyl)benzenesulfonylureas

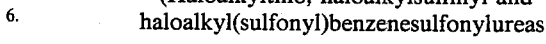

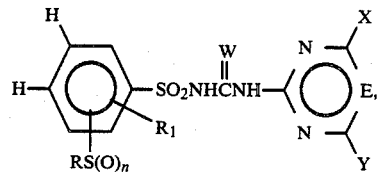

III wherein the substituents are defined as for compound (I).

(Haloalkylthio, haloalkylsulfinyl and haloalkylsulfonyl)benzene derivatives 8a and 8b as starting materials for preparation of III, can be made by known methods [e.g. Chem. Abstr. 70, 96324c (1969); Chem. Abstr. 72, 66651f (1970); England, loc. cit.; Yagupol kii, loc. cit.].

The (trifluoroethylthio)benzenes can be made by reaction of the thiophenol compounds with a trifluoroethylating agent, such as trifluoroethyl iodide or trifluoroethyl trichloromethanesulfonate. The thiophenol compound is reacted with powdered potassium hydroxide and trifluoroethyl iodide in an aprotic solvent such as DMF, dioxane or THF. The reaction proceeds to completion at ambient temperature. Heat (e.g., with a steam bath) may be applied to increase the reaction rate. The product is isolated as described in reaction (a).

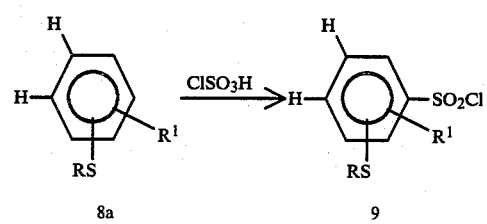

7.

Chlorosulfonation of 8a proceeds in the same manner as described for reaction 1 for the oxygen analog 1.

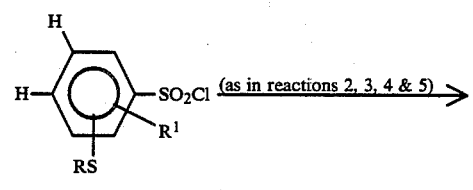

8.

Conversion of the sulfonyl chloride sequentially to the amide, the isocyanate of isothiocyanate, and the sulfonylurea or sulfonylthiourea, proceeds as described for the oxygen analogs in reactions 2, 3, 4 and 5.

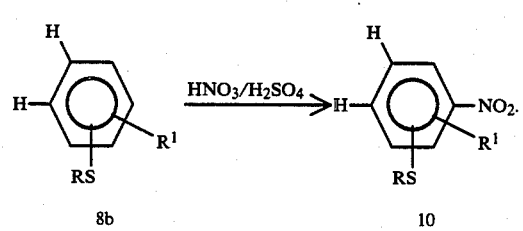

9.

The nitration is conveniently carried out by slow addition of slightly more than 1 equivalent of 90% nitric acid to a stirred, cooled (10°-30°) mixture of the sulfide 8b in sulfuric acid, stirring for an additional 10-45 minutes, pouring the reaction mixture into ice water, extracting the nitro compound into a water-immiscible organic solvent (e.g., 1-chlorobutane or methylene chloride), and evaporating the solution to leave residual nitro compound, which may be further purified by vacuum distillation. Thus, the reaction is a simple mononitration of a substituted benzene ring, a reaction well known in the art.

As mentioned for the oxygen analog, nitration of 8b can lead to isomeric nitro compounds which, likewise, can be separated or used as such.

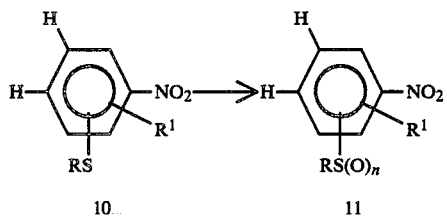

The sulfide 10 is oxidized to the sulfoxide (e.g. with 20-30% $H_2O_2$ in acetic acid, 1-2 hours at 90°-100°); or the sulfide 10 is oxidized to the sulfone [e.g. with chromium trioxide in acetic acid at 90°-110° during $\frac{1}{2}$-2 hours]. See Chem. Abstr. 70, 96324c (1969). If no oxidizing agent is used, n remains at zero and 10=11.

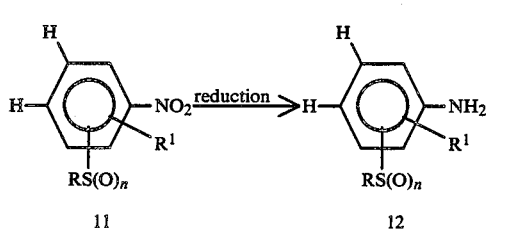

Reduction of nitrobenzene derivatives to nitroaniline derivatives is well known in the art [e.g., W. J. Hickinbottom, "Reactions of Organic Compounds," 452-459, Longmans, London, 1959]. For example, the reduction can be accomplished by the portionwise addition of powdered iron to a mixture of the nitro compound in aqueous acetic acid at 60°-110°; followed by dilution of the reaction mixture with water and filtering off, extracting or, when n=0, steam-distilling the aniline product. Aminothiophenols can be directly tetrahaloethylated or hexafluoropropylated on the chalcogen with tetrahaloethylene or hexafluoropropene to provide directly compounds 12 with n=0 (England et al., loc. cit.; Chem. Abstr. 73, 36584q). Also, compound 12a is commercially available (Aldrich Chemical Co., Milwaukee, Wisc.):

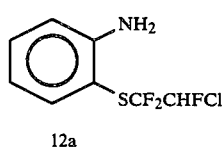

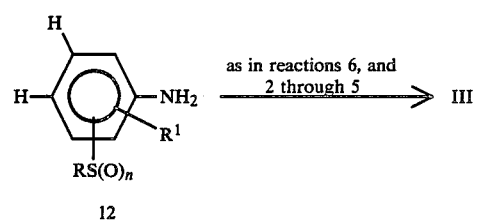

The aniline derivative 12 is diazotized and converted to the sulfonyl chloride, sulfonamide, sulfonyl isocyanate or isothiocyanate and sulfonylurea or sulfonylthiourea as described for reactions 6 and 2 through 5.

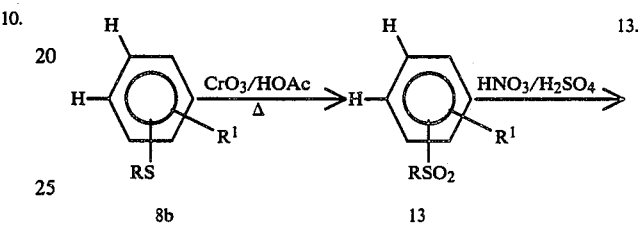

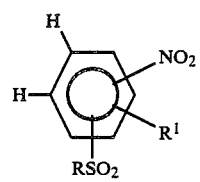

As an alternate method for preparation of the intermediate nitrosulfone (11a), the sulfide 8b is oxidized, as described for reaction 10, to the sulfone 13, followed by nitration to the nitrosulfone 11a. Nitration is accomplished with 90% nitric acid in 20% oleum at 90°-100°, the nitro group joining the ring meta to the haloalkylsulfonyl group [Chem. Abstr. 53, 21766a (1959)]. The nitrosulfone 11a is converted to the sulfonylurea or sulfonylthiourea as already described (Reactions 11, 6 and 2 through 5).

Exemplary compounds within structure (I) that can be made by one or more of the described methods are listed in Table I. Structure IV, as defined below, represents compounds useful as intermediates to compounds of structure (I). Exemplary compounds within structure IV that can be made by one or more of the described methods are listed in Table II.

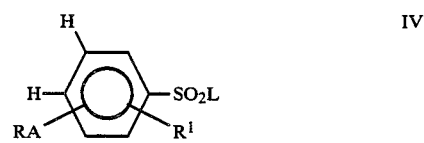

wherein the substituents R, A and $R^1$ are defined as for Formula (I), and L is Cl, $NH_2$, —NCO or —NCS. These lists are not to be considered as limiting, but merely exemplary.

TABLE I

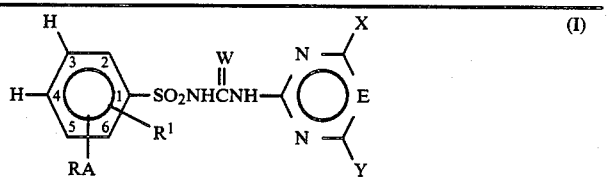

| RA | R¹ | W | E | X | Y | m.p. |
|---|---|---|---|---|---|---|
| 2-CF$_3$O | 5-Cl | O | CH | CH$_3$ | CH$_3$ | |
| 5-CF$_3$O | 2-Cl | O | CH | CH$_3$ | CH$_3$ | |
| 2-HCF$_2$CF$_2$O | 5-Cl | O | CH | CH$_3$ | CH$_3$ | |
| 5-HCF$_2$CF$_2$O | 2-Cl | O | CH | CH$_3$ | CH$_3$ | } 173–177° |
| 2-HCFClCF$_2$O | 5-Cl | O | CH | CH$_3$ | CH$_3$ | |
| 5-HCFClCF$_2$O | 2-Cl | O | CH | CH$_3$ | CH$_3$ | |
| 2-HCFBrCF$_2$O | 5-Cl | O | CH | CH$_3$ | CH$_3$ | } 171–172° (dec) |
| 5-HCFBrCF$_2$O | 2-Cl | O | CH | CH$_3$ | CH$_3$ | |
| 2-CF$_3$CH$_2$O | 5-Cl | O | CH | CH$_3$ | CH$_3$ | |
| 5-CF$_3$CH$_2$O | 2-Cl | O | CH | CH$_3$ | CH$_3$ | |
| 2-CF$_3$O | 5-Br | O | CH | CH$_3$ | CH$_3$ | |
| 5-CF$_3$O | 2-Br | O | CH | CH$_3$ | CH$_3$ | |
| 2-CF$_3$O | 5-F | O | CH | CH$_3$ | CH$_3$ | |
| 5-CF$_3$O | 2-F | O | CH | CH$_3$ | CH$_3$ | |
| 2-HCF$_2$CF$_2$O | 5-CH$_3$ | O | CH | CH$_3$ | CH$_3$ | |
| 5-HCF$_2$CF$_2$O | 2-CH$_3$ | O | CH | CH$_3$ | CH$_3$ | |
| 2-CF$_3$O | 5-Cl | S | CH | CH$_3$ | CH$_3$ | |
| 5-CF$_3$O | 2-Cl | S | CH | CH$_3$ | CH$_3$ | |
| 2-CF$_3$O | 5-Cl | S | N | OCH$_3$ | OCH$_3$ | |
| 5-CF$_3$O | 2-Cl | S | N | OCH$_3$ | OCH$_3$ | |
| 3-CF$_3$O | H | O | CH | CH$_3$ | CH$_3$ | |
| 6-CF$_2$HCF$_2$O | 2-Cl | O | CH | CH$_3$ | CH$_3$ | |
| 2-CF$_2$HCF$_2$O | H | O | CH | CH$_3$ | CH$_3$ | 190–193° |
| 2-CF$_2$HCF$_2$O | H | O | N | OCH$_3$ | CH$_3$ | 180–183° |
| 2-CF$_2$HCF$_2$O | H | O | CH | OCH$_3$ | OCH$_3$ | 172–175° |
| 2-CF$_3$O | 5-Cl | O | CH | CH$_3$ | OCH$_3$ | |
| 5-CF$_3$O | 2-Cl | O | CH | CH$_3$ | OCH$_3$ | |
| 2-CF$_3$O | 5-Cl | O | CH | OCH$_3$ | OCH$_3$ | |
| 5-CF$_3$O | 2-Cl | O | CH | OCH$_3$ | OCH$_3$ | |
| 2-CF$_3$O | 5-Cl | O | CH | OCH$_3$ | CH$_2$OCH$_3$ | |
| 5-CF$_3$O | 2-Cl | O | CH | OCH$_3$ | CH$_2$OCH$_3$ | |
| 2-CF$_3$O | 5-Cl | O | CH | OCH$_3$ | CH$_2$CH$_2$OCH$_3$ | |
| 5-CF$_3$O | 2-Cl | O | CH | OCH$_3$ | CH$_2$CH$_2$OCH$_3$ | |
| 2-CF$_3$O | 5-Cl | O | CH | CH$_3$ | OCH$_2$CO$_2$CH$_3$ | |
| 5-CF$_3$O | 2-Cl | O | CH | CH$_3$ | OCH$_2$CO$_2$CH$_3$ | |
| 2-CF$_3$O | 5-Cl | O | CH | CH$_3$ | OCH$_2$CO$_2$C$_2$H$_5$ | |
| 5-CF$_3$O | 2-Cl | O | CH | CH$_3$ | OCH$_2$CO$_2$C$_2$H$_5$ | |
| 2-CF$_3$O | 5-Cl | O | CH | CH$_3$ | OCHCH$_3$CO$_2$CH$_3$ | |
| 5-CF$_3$O | 2-Cl | O | CH | CH$_3$ | OCHCH$_3$CO$_2$CH$_3$ | |
| 2-CF$_3$O | 5-Cl | O | CH | CH$_3$ | OCHCH$_3$CO$_2$C$_2$H$_5$ | |
| 5-CF$_3$O | 2-Cl | O | CH | CH$_3$ | OCHCH$_3$CO$_2$C$_2$H$_5$ | |
| 2-CF$_3$O | 5-Cl | O | CH | CH$_3$ | OCH$_2$CH$_2$OMe | |
| 5-CF$_3$O | 2-Cl | O | CH | CH$_3$ | OCH$_2$CH$_2$OMe | |
| 2-CF$_3$O | 5-Cl | O | CH | CH$_3$ | OC$_2$H$_5$ | |
| 5-CF$_3$O | 2-Cl | O | CH | CH$_3$ | OC$_2$H$_5$ | |
| 2-CF$_3$O | 5-Cl | O | N | CH$_3$ | CH$_3$ | |
| 5-CF$_3$O | 2-Cl | O | N | CH$_3$ | CH$_3$ | |
| 2-CF$_3$O | 5-Cl | O | N | CH$_3$ | OCH$_3$ | |
| 5-CF$_3$O | 2-Cl | O | N | CH$_3$ | OCH$_3$ | |
| 2-CF$_3$O | 5-Cl | O | N | OCH$_3$ | OCH$_3$ | |
| 5-CF$_3$O | 2-Cl | O | N | OCH$_3$ | OCH$_3$ | |
| 2-CF$_3$O | 5-Cl | O | N | OCH$_3$ | CH$_2$OCH$_3$ | |
| 5-CF$_3$O | 2-Cl | O | N | OCH$_3$ | CH$_2$OCH$_3$ | |
| 2-CF$_3$O | 5-Cl | O | N | OCH$_3$ | CH$_2$CH$_2$OCH$_3$ | |
| 2-CF$_3$CH$_2$O | H | O | CH | CH$_3$ | CH$_3$ | 203–205° (dec) |
| 2-HCFClCF$_2$O | H | O | CH | CH$_3$ | CH$_3$ | |
| 2-HCFBrCF$_2$O | H | O | CH | CH$_3$ | CH$_3$ | |
| 5-CF$_3$O | 2-Cl | O | N | OCH$_3$ | CH$_2$CH$_2$OCH$_3$ | |
| 2-CF$_3$O | 5-Cl | O | N | CH$_3$ | OCH$_2$CO$_2$CH$_3$ | |
| 5-CF$_3$O | 2-Cl | O | N | CH$_3$ | OCH$_2$CO$_2$CH$_3$ | |
| 2-CF$_3$O | 5-Cl | O | N | CH$_3$ | OCH$_2$CO$_2$C$_2$H$_5$ | |
| 5-CF$_3$O | 2-Cl | O | N | CH$_3$ | OCH$_2$CO$_2$C$_2$H$_5$ | |
| 2-CF$_3$O | 5-Cl | O | N | CH$_3$ | OCHCH$_3$CO$_2$CH$_3$ | |
| 5-CF$_3$O | 2-Cl | O | N | CH$_3$ | OCHCH$_3$CO$_2$CH$_3$ | |
| 2-CF$_3$O | 5-Cl | O | N | CH$_3$ | OCHCH$_3$CO$_2$C$_2$H$_5$ | |
| 5-CF$_3$O | 2-Cl | O | N | CH$_3$ | OCHCH$_3$CO$_2$C$_2$H$_5$ | |
| 2-CF$_3$O | 5-Cl | O | N | CH$_3$ | OCH$_2$CH$_2$OCH$_3$ | |
| 5-CF$_3$O | 2-Cl | O | N | CH$_3$ | OCH$_2$CH$_2$OCH$_3$ | |
| 2-CF$_3$O | 5-Cl | O | N | CH$_3$ | OC$_2$H$_5$ | |
| 5-CF$_3$O | 2-Cl | O | N | CH$_3$ | OC$_2$H$_5$ | |

TABLE I-continued (I) Structure: benzene ring with H at 3, H at 4, RA at 5, R¹ at 6, SO₂NHC(=W)NH- at 1, connected to heterocycle with N, N, E, X, Y substituents.

| RA | R¹ | W | E | X | Y | m.p. |
|---|---|---|---|---|---|---|
| 2-CF₃S | 5-Cl | O | CH | CH₃ | CH₃ | |
| 5-CF₃S | 2-Cl | O | CH | CH₃ | CH₃ | |
| 2-CF₃S(O) | 5-Cl | O | CH | CH₃ | CH₃ | |
| 5-CF₃S(O) | 2-Cl | O | CH | CH₃ | CH₃ | |
| 5-CF₃SO₂ | 2-Cl | O | CH | CH₃ | CH₃ | |
| 3-CF₃SO₂ | H | O | CH | CH₃ | CH₃ | |
| 2-CF₃S(O) | H | O | CH | CH₃ | CH₃ | |
| 2-CF₃SO₂ | H | O | CH | CH₃ | CH₃ | |
| 2-CF₃S | H | O | CH | CH₃ | CH₃ | |
| 2-CF₂HCF₂S | H | O | CH | CH₃ | CH₃ | 196° (dec) |
| 2-CFClHCF₂S | H | O | CH | CH₃ | CH₃ | |
| 2-CFBrHCF₂S | H | O | CH | CH₃ | CH₃ | |
| 2-CF₂HCF₂S(O) | H | O | CH | CH₃ | CH₃ | |
| 2-CF₂HCF₂SO₂ | H | O | CH | CH₃ | CH₃ | |
| 2-HCF₂O | H | O | CH | CH₃ | CH₃ | |
| 2-CF₃CHFCF₂O | H | O | CH | CH₃ | CH₃ | 177–178° |
| 2-CF₃CHFCF₂O | H | O | N | OCH₃ | CH₃ | 154–157° |
| 2-CF₃CHFCF₂O | H | O | CH | OCH₃ | OCH₃ | 189° |
| 2-CF₃CHFCF₂O | H | O | CH | OCH₃ | CH₃ | 169–170° |
| 2-HCFBrCF₂O | 5-Br | O | CH | CH₃ | CH₃ | } 181–183° (dec) |
| 5-HCFBrCF₂O | 2-Br | O | CH | CH₃ | CH₃ | |
| 2-CF₂HCF₂S | 5-Cl | O | CH | CH₃ | CH₃ | } 191–193° (dec) |
| 5-CF₂HCF₂S | 2-Cl | O | CH | CH₃ | CH₃ | |
| 2-CF₂HCF₂O | 6-CH₃ | O | CH | CH₃ | CH₃ | 198° (dec) |
| 2-CHF₂S | H | O | CH | CH₃ | CH₃ | |
| 2-CHF₂S(O) | H | O | CH | CH₃ | CH₃ | |
| 2-CHF₂SO₂ | H | O | CH | CH₃ | CH₃ | |
| 2-CF₃CHFCF₂S | H | O | CH | CH₃ | CH₃ | |
| 2-CF₃CHFCF₂S(O) | H | O | CH | CH₃ | CH₃ | |
| 2-CF₃CHFCF₂SO₂ | H | O | CH | CH₃ | CH₃ | |
| 2-HCF₂O | H | O | CH | OCH₃ | OCH₃ | 167–168.5° |

TABLE II

Structure IV: benzene ring with H at 3, H at 4, RA at 5, R¹ at 6, SO₂L at 1.

| RA | R¹ | L |
|---|---|---|
| 2-CF₃O | 5-Cl | Cl |
| 5-CF₃O | 2-Cl | Cl |
| 2-HCF₂CF₂O | 5-Cl | Cl |

TABLE II-continued

| RA | R¹ | L | |
|---|---|---|---|
| 5-HCF₂CF₂O | 2-Cl | Cl | |
| 2-HCFClCF₂O | 5-Cl | Cl | } oil |

TABLE II-continued

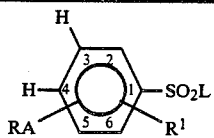

IV

| RA | R¹ | L | |
|---|---|---|---|
| 5-HCFClCF$_2$O | 2-Cl | Cl | |
| 2-HCFBrCF$_2$O | 5-Cl | Cl | } oil |
| 5-HCFBrCF$_2$O | 2-Cl | Cl | |
| 2-CF$_3$CH$_2$O | 5-Cl | Cl | |
| 5-CF$_3$CH$_2$O | 2-Cl | Cl | |
| 2-CF$_3$O | 5-Br | Cl | |
| 5-CF$_3$O | 2-Br | Cl | |
| 2-CF$_3$O | 5-F | Cl | |
| 5-CF$_3$O | 2-F | Cl | |
| 2-HCF$_2$CF$_2$O | 5-CH$_3$ | Cl | |
| 5-HCF$_2$CF$_2$O | 2-CH$_3$ | Cl | |
| 2-CF$_2$HCF$_2$O | H | Cl | |
| 2-CF$_3$CH$_2$O | H | Cl | solid |
| 2-HCFClCF$_2$O | H | Cl | |
| 2-HCFBrCF$_2$O | H | Cl | |
| 2-CF$_3$S | 5-Cl | Cl | |
| 5-CF$_3$S | 2-Cl | Cl | |
| 2-CF$_3$S(O) | 5-Cl | Cl | |
| 5-CF$_3$S(O) | 2-Cl | Cl | |
| 5-CF$_3$SO$_2$ | 2-Cl | Cl | |
| 2-CF$_3$S | H | Cl | |
| 2-CF$_3$S(O) | H | Cl | |
| 2-CF$_3$SO$_2$ | H | Cl | |
| 2-HCF$_2$CF$_2$S | H | Cl | |
| 2-HCF$_2$CF$_2$S(O) | H | Cl | |
| 2-HCF$_2$CF$_2$SO$_2$ | H | Cl | |
| 2-HCFClCF$_2$S | H | Cl | |
| 2-HCFBrCF$_2$S | H | Cl | |
| 2-HCF$_2$CF$_2$S | 5-Cl | Cl | } oil |
| 5-HCF$_2$CF$_2$S | 2-Cl | Cl | |
| 2-HCF$_2$O | H | Cl | oil |
| 2-CF$_3$CHFCF$_2$O | H | Cl | oil |
| 2-HCF$_2$S | H | Cl | |
| 2-HCF$_2$S(O) | H | Cl | |
| 2-HCF$_2$SO$_2$ | H | Cl | |
| 2-CF$_3$CHFCF$_2$S | H | Cl | |
| 2-CF$_3$CHFCF$_2$S(O) | H | Cl | |
| 2-CF$_3$CHFCF$_2$SO$_2$ | H | Cl | |
| 2-HCF$_2$CF$_2$O | 5-Br | Cl | } oil, bp 83–103/0.1 Torr |
| 5-HCF$_2$CF$_2$O | 2-Br | Cl | |
| 2-HCF$_2$CF$_2$O | 6-CH$_3$ | Cl | oil |
| 2-CF$_3$O | 5-Cl | NH$_2$ | |
| 5-CF$_3$O | 2-Cl | NH$_2$ | |
| 2-HCF$_2$CF$_2$O | 5-Cl | NH$_2$ | |
| 5-HCF$_2$CF$_2$O | 2-Cl | NH$_2$ | |
| 2-HCFClCF$_2$O | 5-Cl | NH$_2$ | } 124–126° |
| 5-HCFClCF$_2$O | 2-Cl | NH$_2$ | |

TABLE II-continued

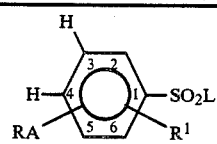

IV

| RA | R¹ | L | |
|---|---|---|---|
| 2-HCFBrCF$_2$O | 5-Cl | NH$_2$ | } 86–90° and 101–103° |
| 5-HCFBrCF$_2$O | 2-Cl | NH$_2$ | |
| 2-CF$_3$CH$_2$O | 5-Cl | NH$_2$ | |
| 5-CF$_3$CH$_2$O | 2-Cl | NH$_2$ | |
| 2-CF$_3$O | 5-Br | NH$_2$ | |
| 5-CF$_3$O | 2-Br | NH$_2$ | |
| 2-CF$_3$O | 5-F | NH$_2$ | |
| 5-CF$_3$O | 2-F | NH$_2$ | |
| 2-HCF$_2$CF$_2$O | 5-CH$_3$ | NH$_2$ | |
| 5-HCF$_2$CF$_2$O | 2-CH$_3$ | NH$_2$ | |
| 2-CF$_2$HCF$_2$O | H | NH$_2$ | 118–120° |
| 2-CF$_3$CH$_2$O | H | NH$_2$ | 127–129° |
| 2-HCFClCF$_2$O | H | NH$_2$ | |
| 2-HCFBrCF$_2$O | H | NH$_2$ | |
| 2-CF$_3$S | 5-Cl | NH$_2$ | |
| 5-CF$_3$S | 2-Cl | NH$_2$ | |
| 2-CF$_3$S(O) | 5-Cl | NH$_2$ | |
| 5-CF$_3$S(O) | 2-Cl | NH$_2$ | |
| 5-CF$_3$SO$_2$ | 2-Cl | NH$_2$ | |
| 2-CF$_3$S | H | NH$_2$ | |
| 2-CF$_3$S(O) | H | NH$_2$ | |
| 2-CF$_3$SO$_2$ | H | NH$_2$ | |
| 2-HCF$_2$CF$_2$S | H | NH$_2$ | |
| 2-HCF$_2$CF$_2$S(O) | H | NH$_2$ | |
| 2-HCF$_2$CF$_2$SO$_2$ | H | NH$_2$ | |
| 2-HCFClCF$_2$S | H | NH$_2$ | 99–101° |
| 2-HCFBrCF$_2$S | H | NH$_2$ | |
| 2-HCF$_2$CF$_2$S | 5-Cl | NH$_2$ | } 96–100° |
| 5-HCF$_2$CF$_2$S | 2-Cl | NH$_2$ | |
| 2-HCF$_2$O | H | NH$_2$ | 130–134° |
| 2-CF$_3$CHFCF$_2$O | H | NH$_2$ | 94–96° |
| 2-HCF$_2$S | H | NH$_2$ | |
| 2-HCF$_2$S(O) | H | NH$_2$ | |
| 2-HCF$_2$SO$_2$ | H | NH$_2$ | |
| 2-CF$_3$CHFCF$_2$S | H | NH$_2$ | |
| 2-CF$_3$CHFCF$_2$S(O) | H | NH$_2$ | |
| 2-CF$_3$CHFCF$_2$SO$_2$ | H | NH$_2$ | |
| 2-HCF$_2$CF$_2$O | 5-Br | NH$_2$ | } 99–117° |
| 5-HCF$_2$CF$_2$O | 2-Br | NH$_2$ | |
| 2-HCF$_2$CF$_2$O | 6-CH$_3$ | NH$_2$ | 104–105° |
| 2-CF$_3$O | 5-Cl | —NCO | |
| 5-CF$_3$O | 2-Cl | —NCO | |
| 2-HCF$_2$CF$_2$O | 5-Cl | —NCO | |
| 5-HCF$_2$CF$_2$O | 2-Cl | —NCO | |
| 2-HCFClCF$_2$O | 5-Cl | —NCO | } oil |
| 5-HCFClCF$_2$O | 2-Cl | —NCO | |
| 2-HCFBrCF$_2$O | 5-Cl | —NCO | |

TABLE II-continued

Structure IV: benzene ring with positions 1-6; position 1 has $SO_2L$, position 2 has $R^1$, position 4 has RA, positions 3, 5, 6 have H (with position 4 labeled RA and position 6 labeled $R^1$ in structure).

| RA | $R^1$ | L | |
|---|---|---|---|
| 5-HCFBrCF$_2$O | 2-Cl | —NCO | } oil |
| 2-CF$_3$CH$_2$O | 5-Cl | —NCO | |
| 5-CF$_3$CH$_2$O | 2-Cl | —NCO | |
| 2-CF$_3$O | 5-Br | —NCO | |
| 5-CF$_3$O | 2-Br | —NCO | |
| 2-CF$_3$O | 5-F | —NCO | |
| 5-CF$_3$O | 2-F | —NCO | |
| 2-HCF$_2$CF$_2$O | 5-CH$_3$ | —NCO | |
| 5-HCF$_2$CF$_2$O | 2-CH$_3$ | —NCO | |
| 2-CF$_2$HCF$_2$O | H | —NCO | |
| 2-CF$_3$CH$_2$O | H | —NCO | oil |
| 2-HCFClCF$_2$O | H | —NCO | |
| 2-HCFBrCF$_2$O | H | —NCO | |
| 2-CF$_3$S | 5-Cl | —NCO | |
| 5-CF$_3$S | 2-Cl | —NCO | |
| 2-CF$_3$S(=O) | 5-Cl | —NCO | |
| 5-CF$_3$S(=O) | 2-Cl | —NCO | |
| 5-CF$_3$SO$_2$ | 2-Cl | —NCO | |
| 2-CF$_3$S | H | —NCO | |
| 2-CF$_3$S(=O) | H | —NCO | |
| 2-CF$_3$SO$_2$ | H | —NCO | |
| 2-HCF$_2$CF$_2$S | H | —NCO | |
| 2-HCF$_2$CF$_2$S(=O) | H | —NCO | |
| 2-HCF$_2$CF$_2$SO$_2$ | H | —NCO | |
| 2-HCFClCF$_2$S | H | —NCO | oil |
| 2-HCFBrCF$_2$S | H | —NCO | |
| 2-HCF$_2$CF$_2$O | 5-Br | —NCO | } oil |
| 5-HCF$_2$CF$_2$O | 2-Br | —NCO | |
| 2-HCF$_2$O | H | —NCO | oil |
| 2-CF$_3$CHFCF$_2$O | H | —NCO | oil |
| 2-HCF$_2$S | H | —NCO | |
| 2-HCF$_2$S(=O) | H | —NCO | |
| 2-HCF$_2$SO$_2$ | H | —NCO | |
| 2-CF$_3$CHFCF$_2$S | H | —NCO | |
| 2-CF$_3$CHFCF$_2$S(=O) | H | —NCO | |
| 2-CF$_3$CHFCF$_2$SO$_2$ | H | —NCO | |
| 2-HCF$_2$CF$_2$S | 5-Cl | —NCO | } oil |
| 5-HCF$_2$CF$_2$S | 2-Cl | —NCO | |
| 2-HCF$_2$CF$_2$O | 6-CH$_3$ | —NCO | oil |
| 2-CF$_3$O | 5-Cl | —NCS | |
| 5-CF$_3$O | 2-Cl | —NCS | |
| 2-HCF$_2$CF$_2$O | 5-Cl | —NCS | |
| 5-HCF$_2$CF$_2$O | 2-Cl | —NCS | |
| 2-HCFClCF$_2$O | 5-Cl | —NCS | |
| 5-HCFClCF$_2$O | 2-Cl | —NCS | |
| 2-HCFBrCF$_2$O | 5-Cl | —NCS | |
| 5-HCFBrCF$_2$O | 2-Cl | —NCS | |
| 2-CF$_3$CH$_2$O | 5-Cl | —NCS | |
| 5-CF$_3$CH$_2$O | 2-Cl | —NCS | |
| 2-CF$_3$O | 5-Br | —NCS | |
| 5-CF$_3$O | 2-Br | —NCS | |
| 2-CF$_3$O | 5-F | —NCS | |
| 5-CF$_3$O | 2-F | —NCS | |
| 2-HCF$_2$CF$_2$O | 5-CH$_3$ | —NCS | |
| 5-HCF$_2$CF$_2$O | 2-CH$_3$ | —NCS | |
| 2-CF$_2$HCF$_2$O | H | —NCS | |
| 2-CF$_3$CH$_2$O | H | —NCS | |
| 2-HCFClCF$_2$O | H | —NCS | |
| 2-HCFBrCF$_2$O | H | —NCS | |
| 2-CF$_3$S | 5-Cl | —NCS | |
| 5-CF$_3$S | 2-Cl | —NCS | |
| 2-CF$_3$S(=O) | 5-Cl | —NCS | |
| 5-CF$_3$S(=O) | 2-Cl | —NCS | |
| 5-CF$_3$SO$_2$ | 2-Cl | —NCS | |
| 2-CF$_3$S | H | —NCS | |
| 2-CF$_3$S(=O) | H | —NCS | |
| 2-CF$_3$SO$_2$ | H | —NCS | |
| 2-HCF$_2$CF$_2$S | H | —NCS | |
| 2-HCF$_2$CF$_2$S(=O) | H | —NCS | |
| 2-HCF$_2$CF$_2$SO$_2$ | H | —NCS | |
| 2-HCFClCF$_2$S | H | —NCS | |
| 2-HCFBrCF$_2$S | H | —NCS | |
| 2-HCF$_2$O | H | —NCS | |
| 2-CF$_3$CHFCF$_2$O | H | —NCS | |
| 2-HCF$_2$S | H | —NCS | |
| 2-HCF$_2$S(=O) | H | —NCS | |
| 2-HCF$_2$SO$_2$ | H | —NCS | |
| 2-CF$_3$CHFCF$_2$S | H | —NCS | |
| 2-CF$_3$CHFCF$_2$S(=O) | H | —NCS | |
| 2-CF$_3$CHFCF$_2$SO$_2$ | H | —NCS | |

In the examples which follow, all parts and percentages are by weight and all temperatures in degrees centigrade unless specified otherwise. The examples are not to be considered as limiting, but merely exemplary of the methods which can be used to prepare the compounds of this invention.

EXAMPLE 1

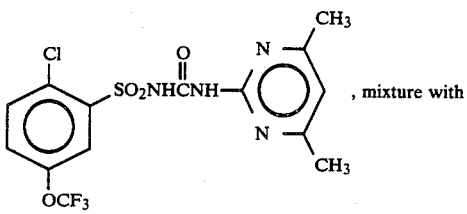, mixture with

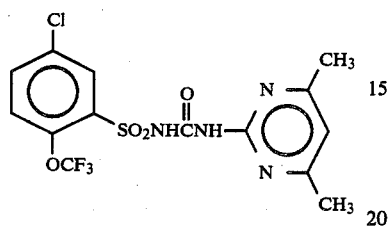

a. Into 49.1 g (0.25 mole) of 1-chloro-4-(trifluoromethoxy)benzene was dripped 82 ml (1.25 mole) of chlorosulfonic acid at 20°–25°. The mixture was stirred for a day, then cooled to −10° and poured slowly onto excess, stirred ice. The mixture was extracted with butyl chloride and the butyl chloride extracts washed with water, dilute sodium bicarbonate solution, and saturated brine, dried with MgSO$_4$, and evaporated in vacuo to an orange oil. Vacuum distillation of the oil provided the product as an oil, bp 114°–116°/8 Torr, starting material and some haloformate by-product. The oil was an isomeric mixture comprising the two isomers:

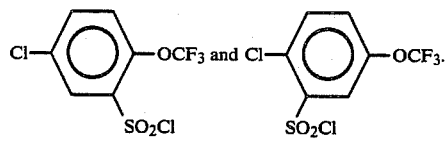

b. A solution of 26.5 g of the mixed sulfonyl chlorides in 200 ml of THF was gassed with excess ammonia at ≦30°, then evaporated and the residue treated with water and ethyl acetate. The ethyl acetate solution was washed with saturated brine, dried, concentrated to 50 ml, and diluted with hexane to provide 20 g (81%) of the product as a white solid, m.p. 93°–96° (partial) and 103°–105° (remainder). The product was an isomeric mixture of the two isomers:

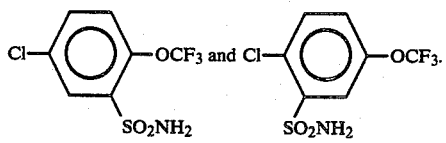

c. To 10 g of the mixed sulfonamides was added 70 ml of thionyl chloride and the mixture boiled under reflux for 20 hours. The thionyl chloride was stripped and the residual oil dissolved in 50 ml of toluene. To the solution was added 0.3 ml of pyridine and 6 ml of liquid phosgene. The resulting mixture was heated at 85°–90° for 2 hours under phosgene reflux. The cooled mixture was filtered and stripped to a residual oil, which was the mixed-isomer sulfonyl isocyanate (IR spectrum: strong absorption at 2240 cm$^{-1}$). The oil was dissolved in 100 ml of acetonitrile and reacted with 4.4 g of 2-amino-4,6-dimethylpyrimidine. An exothermic reaction ensued, with precipitation of white solid. After 1.5 hours, the white solid was filtered off and washed with acetonitrile and ether, providing the title sulfonylurea isomeric mixture, m.p. 195°–199° (dec.).

Anal. Calcd. for $C_{14}H_{12}ClF_3N_4O_4S$: C, 39.6; H, 2.8; Cl, 8.3; S, 7.5; Found: C, 39.6; H, 2.9; Cl, 8.2; S, 7.9.

EXAMPLE 2

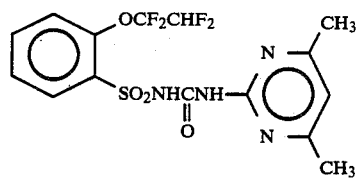

a. A stirred mixture of 20.9 g of 2-(1,1,2,2-tetrafluoroethoxy)benzenesulfonamide, 10 g of butyl isocyanate, 50 mg of 1,4-diazabicyclo[2.2.2]octane and 140 ml of xylene was boiled under reflux for 0.5 hour. Phosgene gas was then passed into the system under a dry-ice reflux condenser, causing the reaction temperature to fall to 120°. Phosgene addition was continued until the reaction temperature would not rise above 120°; at this point, phosgene addition was stopped. The reaction temperature was raised to 136° by removal of the dry-ice condenser and allowing phosgene to escape to a scrubber, then lowered to 25°; the mixture was then filtered. The filtrate was evaporated in vacuum to provide 2-(1,1,2,2-tetrafluoroethoxy)benzenesulfonyl isocyanate as an oil (strong absorption at 2225 cm$^{-1}$ in the infrared spectrum, for the isocyanate), which can be further purified by vacuum distillation.

b. Into a stirred solution of the 2-(1,1,2,2-tetrafluoroethoxy)benzenesulfonyl isocyanate in 200 ml of acetonitrile was added 12.3 g of 2-amino-4,6-dimethylpyrimidine and the mixture stirred overnight (about 15 hours). The mixture was cooled, diluted with diethyl ether and the solid washed with cold acetonitrile and diethyl ether, then vacuum-dried, providing the title sulfonylurea as a white solid, m.p. 190°–193° (dec.).

EXAMPLE 3

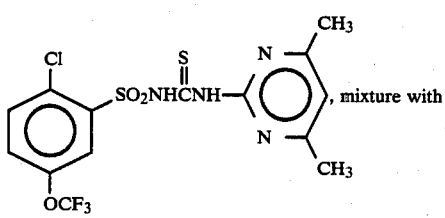, mixture with

-continued

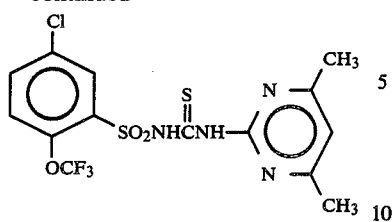

The mixed-isomer sulfonamide, 27.6 g, obtained in Example 1c, is dissolved in 100 ml of DMF and is treated with 7.6 g of carbon disulfide and 6.6 g of powdered 85% potassium hydroxide. The mixture is stirred at about 35° until dissolution is completed, and again treated with the same amount of potassium hydroxide and stirred until dissolution is completed. The mixture is treated with excess ethyl acetate, added dropwise to precipitate the intermediate, which is vacuum-dried.

The intermediate is suspended in toluene and reacted at 5°–10° with 20 g of phosgene. After 2 hours at room temperature, the mixture is filtered and stripped to residual sulfonyl isothiocyanate.

A solution of 14.3 g of sulfonyl isothiocyanate in 100 ml of acetonitrile is reacted with 6.2 g of 2-amino-4,6-dimethylpyrimidine and the mixture is stirred overnight. Dilution of the concentrated mixture with ether provides the title sulfonylthioureas as a solid.

EXAMPLE 4

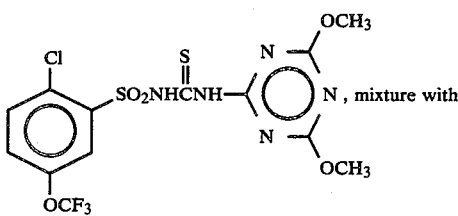

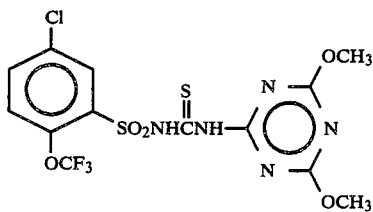

A mixture of 5.5 g of the mixed-isomer sulfonamide, is obtained from example 1, 4.0 g of 4,6-dimethoxy-2-isothiocyanato-1,3,5-triazine and 2.7 g of anhydrous potassium carbonate in 70 ml of acetone is warmed to 40° with stirring. After 2 hours, a thick precipitate is formed and stirring is continued for three more hours at ambient temperature. The precipitate is removed by filtration, suspended in 150 ml of water, stirred and the pH adjusted to 2 by the addition of hydrochloric acid.

The desired product is removed by filtration, washed with cold water and dried to provide the title product.

EXAMPLE 5

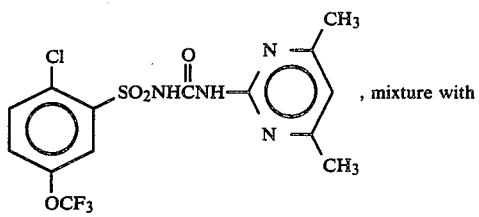
, mixture with

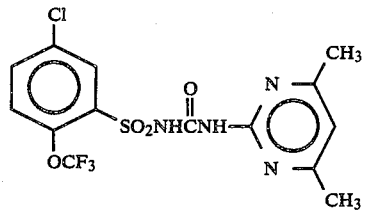

a. A solution of 68.2 g of 1-chloro-(2- and 3-nitro)-4-(trifluoromethoxy)benzene [J. Org. Chem. 29, 1 (1964)] in a mixture of 229 ml of acetic acid and 57 ml of water was treated at 80°–95°, portionwise, with 61 g of powdered iron, an additional 57 ml of water being added after half the iron was added. After an additional 30 minutes heating on a steam bath, the mixture was diluted with water and the product isolated by steam distillation, followed by extraction of the product into butyl chloride, water-washing the butyl chloride extract, evaporation and distillation at 75°–79°/10 Torr. Yield: 56 g. The product, an oil, is a mixture of the two isomers:

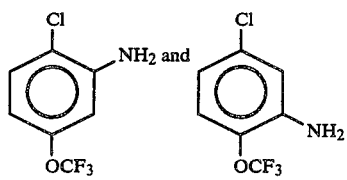

b. The aniline derivative, 56 g, is added to 200 ml of concentrated hydrochloric acid and 60 ml of acetic acid at 0° during 15 minutes. Then a solution of 26 g of sodium nitrite in 70 ml of water is added at 0 to 3° during 45 minutes. After an additional 10 minutes at 0°, the mixture is poured into a mixture of 285 ml of acetic acid, 7 g of cuprous chloride and 50 ml of sulfur dioxide at 5° over 10 minutes. After 15 minutes at 0° to 5°, the mixture is warmed to 25° and kept at 25° for 3 hours. The mixture is poured into 1.5 l of water and the sulfonyl chloride product is extracted into butyl chloride. The butyl chloride solution is washed with water, dilute sodium bicarbonate solution, and saturated brine, then dried (MgSO4). The butyl chloride solution contains the same sulfonyl chlorides described in Example 1a, and can be converted to sulfonylureas or sulfonylthioureas as previously described.

EXAMPLE 6

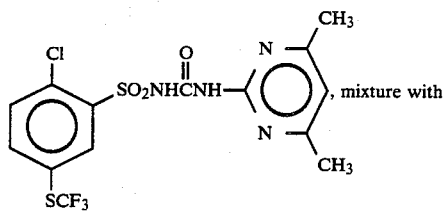, mixture with

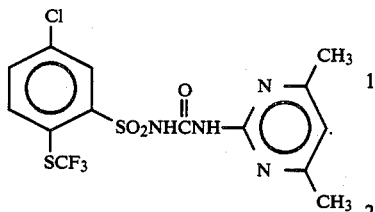

Into 53.2 g of 4-chlorophenyl trifluoromethyl sulfide is dripped 82 ml of chlorosulfonic acid at 20°. After a day, the mixture is poured onto excess ice and extracted with butyl chloride. The butyl chloride extract is washed with water and dilute sodium bicarbonate, and dried. The dried solution of isomeric sulfonyl chlorides is converted to the sulfonamides by gassing with ammonia at 25°, stripping, washing the residue with water and drying in a vacuum oven. The sulfonamides are converted to the sulfonyl isocyanate as described in Example 1c. The sulfonyl isocyanates isomeric mixture is dissolved in 100 ml of acetonitrile and treated with 6.2 g of 2-amino-4,6-dimethylpyrimidine. The mixture is stirred overnight, diluted with butyl chloride and hexane and the title product filtered off and dried.

EXAMPLE 7

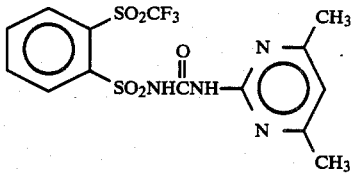

To 74 ml of concentrated hydrochloric acid and 22 ml of acetic acid is added 22.5 g of 2-aminophenyl trifluoromethyl sulfone [Chem. Abstr. 70, 96324c (1969)] at 0° over 15 minutes. A solution of 9.6 g of sodium nitrite in 26 ml of water is added at 0° to 3° over 45 minutes. After an additional 10 minutes at 0°, the reaction mixture is poured into a mixture of 107 ml of acetic acid, 2.6 g of cuprous chloride and 19 ml of sulfur dioxide at 5° over 10 minutes. The mixture is stirred at 0° to 5° for 1 hour and at 25° for 3 hours, then poured into ice water and the sulfonyl chloride extracted into ether. The ether extracts are washed with water, sodium bicarbonate solution until basic, saturated brine, and then dried with MgSO4.

The ether solution is gassed with ammonia at 20°, then stripped. The residue is washed with water and the sulfonamide dried in a vacuum oven.

The sulfonamide is converted to the isocyanate as in Example 1c. The isocyanate is treated in acetonitrile with 12.3 g of 2-amino-4,6-dimethylpyrimidine. After an overnight reaction period, the mixture is diluted with butyl chloride to provide the title sulfonylurea as a white solid.

EXAMPLE 8

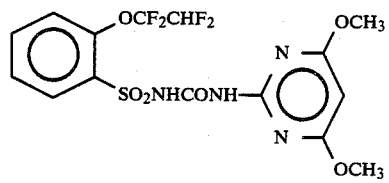

a. Into a cooled (10°) solution of 55 ml of acetic acid and 180 ml concentrated hydrochloric acid was poured 50 g of 2-(1,1,2,2-tetrafluoroethoxy)aniline. The resulting thick mixture was contacted dropwise at 0° to 5° with a solution of 23.5 g of sodium nitrite in 62 ml of water, providing an orange solution containing suspended salt. This diazonium mixture was poured, portionwise, into a stirred, cooled (0° to 5°) mixture of 45 ml SO2 (liquid) in 257 ml of acetic acid. Gas evolution was noted. The mixture was kept at 0° to 5° for 30 minutes, then treated with 300 ml of 1-chlorobutane and 100 ml of hexane and heated to 25° during a 20-minute period. After an additional hour, water was added, the organic layer separated and washed with water (2X) and saturated sodium bicarbonate solution until a basic wash is obtained. The chlorobutane solution was dried over MgSO4, and the filtered mixture evaporated in vacuum to 69.5 g of yellow oil, 2-(1,1,2,2-tetrafluoroethoxy)benzenesulfonyl chloride.

b. The sulfonyl chloride was dissolved in 250 ml of tetrahydrofuran (THF) and contacted at ≦30° with 14.1 ml of ammonia (liquid). After 10 minutes, the THF was evaporated in vacuum and the residual solid treated with water, and the crude sulfonamide filtered off. The sulfonamide was recrystallized from dimethylformamide/water, then 1-chlorobutane/hexane, providing 41.8 g of 2-(1,1,2,2-tetrafluoroethoxy)benzenesulfonamide as a white solid, m.p. 117°-119°. An additional portion of product was recovered from the mother liquor.

c. The 41.8 g of sulfonamide was mixed with 200 ml of thionyl chloride and the mixture boiled under reflux for 22.5 hours. The yellow solution was evaporated in vacuum and the semisolid residue treated with 150 ml of a solution of phosgene (about 15%) in toluene. Five drops of pyridine was added and the mixture heated under a dry-ice reflux condenser; phosgene was allowed to escape to a trap until the reaction temperature reached 85°. After 2 hours at 85°, the mixture was evaporated in vacuum to a residual orange oil and small amounts of solid. The residue was contacted with 1-chlorobutane, the mixture filtered and the filtrate evaporated in vacuum to an orange oil, 2-(1,1,2,2-tetrafluoroethoxy)benzenesulfonyl isocyanate. The isocyanate was dissolved in 200 ml of acetonitrile and contacted with 23.7 g of 2-amino-4,6-dimethoxypyrimidine. A dark coloration immediately ensued, followed by precipitation of solid. After 15 minutes, the mixture was cooled in an ice bath and the solid filtered off. Recrystallization of the solid provided 24.3 g of the title compound as a white solid, m.p. 191°-192°. An additional 6.6 g of the compound, m.p. 189°-190°, was obtained by dilution of the mother liquor with hexane.

Anal. Calcd. for $C_{15}H_{14}F_4N_4O_6S$: C, 39.6; H, 3.1; N, 12.3; S, 7.1. Found: C, 40.1; H, 3.1; N, 12.2; S, 7.5.

FORMULATIONS

Useful formulations of the compounds of Formula (I) can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters per hectare to several hundred liters per hectare. High-strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table III.

TABLE III

|  | Weight Percent* | | |
| --- | --- | --- | --- |
|  | Active Ingredient | Diluent(s) | Surfactant(s) |
| Wettable Powders | 20–90 | 0–74 | 1–10 |
| Oil Suspensions, Solutions, Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules & Pellets | 0.1–95 | 5–99.9 | 0–15 |
| High-Strength Compositions | 90–99 | 0–10 | 0–2 |

*Active ingredient plus at least one of a surfactant or a diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation or by tank mixing.

Some typical diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd. Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer- or fluid-energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147 ff. and "Perry's Chemical Engineer's Handbook", 4th Ed., McGraw-Hill, New York, 1963, pp. 8-59 ff.

For further information regarding the art of formulation, see for example:

- H. M. Loux, U.S. Pat. No. 3,235,361, Col. 6, line 16 through Col. 7, line 19, and Examples 10 through 41.
- R. W. Luckenbaugh, U.S. Pat. No. 3,309,192, Col. 5, line 43 through Col. 7, line 62, and Examples 8, 12, 15, 39, 41, 52, 53, 58, 132, 138–140, 162–164, 166, 167, and 169–182.
- H. Gysin and E. Knusli, U.S. Pat. No. 2,891,855, Col. 3, line 66 through Col. 5, line 17 and Examples 1–4.
- G. C. Klingman, "Weed Control as a Science", John Wiley and Sons, Inc., New York, 1961, pp. 81–96.
- J. D. Fryer and S. A. Evans, "Weed Control Handbook", 5th Ed., Blackwell Scientific Publications, Oxford, 1968, pp. 101–103.

Unless otherwise indicated, all parts are by weight in the following examples.

EXAMPLE 9

| Wettable Powder | |
| --- | --- |
| 5-Chloro-N—[(4,6-dimethylpyrimidin-2-yl)-aminocarbonyl]-2-(trifluoromethoxy)-benzenesulfonamide; and 2-Chloro-N—[(4,6-dimethylpyrimidin-2-yl)-aminocarbonyl]-2-(trifluoromethoxy)-benzenesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended, sifted through a U.S.S. No. 50 sieve (0.3 mm opening) and packaged.

EXAMPLE 10

| Wettable Powder | |
| --- | --- |
| 5-Chloro-N—[(4,6-dimethylpyrimidin-2-yl)-aminocarbonyl]-2-(trifluoromethoxy)-benzenesulfonamide; and 2-Chloro-N—[(4,6-dimethylpyrimidin-2-yl)-aminocarbonyl]-5-(trifluoromethoxy)-benzenesulfonamide | 50% |
| sodium alkylnaphthalenesulfonate | 2% |
| low-viscosity methyl cellulose | 2% |
| diatomaceous earth | 46% |

The ingredients are blended, coarsely hammer milled and then air milled to produce particles of active ingredient all below 10 microns in diameter. The product is reblended before packaging.

EXAMPLE 11

| Granule | |
| --- | --- |
| Wettable powder of Example 10 | 10% |
| attapulgite granules | 90% |

A slurry of wettable powder containing 50% solids is sprayed on the surface of attapulgite granules in a double-cone blender. The granules are dried and packaged.

EXAMPLE 12

| Wettable Powder | |
|---|---|
| 5-Chloro-N—[(4,6-dimethylpyrimidin-2-yl)-aminocarbonyl]-2-(trifluoromethoxy)-benzenesulfonamide; and 2-Chloro-N—[(4,6-dimethylpyrimidin-2-yl)-aminocarbonyl]-5-(trifluoromethoxy)-benzenesulfonamide | 80% |
| sodium alkylnaphthalenesulfonate | 2% |
| sodium ligninsulfonate | 2% |
| synthetic amorphous silicate | 3% |
| kaolinite | 13% |

The ingredients are blended and coarsely ground in a hammer mill to produce particles essentially all below 100 microns in size. The material is reblended, sifted through a U.S.S. No. 50 sieve (0.3 mm opening) and packaged.

EXAMPLE 13

| Extruded Pellet | |
|---|---|
| 5-Chloro-N—[(4,6-dimethylpyrimidin-2-yl)-aminocarbonyl]-2-(trifluoromethoxy)-benzenesulfonamide; and 2-Chloro-N—[(4,6-dimethylpyrimidin-2-yl)-aminocarbonyl]-5-(trifluoromethoxy)-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass through a U.S.S. No. 20 sieve (0.84 mm openings). The granules held on a U.S.S. No. 40 sieve (0.42 mm openings) may be packaged for use and the fines recycled.

EXAMPLE 14

| Oil Suspension | |
|---|---|
| 5-Chloro-N—[(4,6-dimethylpyrimidin-2-yl)-aminocarbonyl]-2-(trifluoromethoxy)-benzenesulfonamide; and 2-Chloro-N—[(4,6-dimethylpyrimidin-2-yl)-aminocarbonyl]-5-(trifluoromethoxy)-benzenesulfonamide | 25% |
| polyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 15

| Wettable Powder | |
|---|---|
| 5-Chloro-N—[(4,6-dimethylpyrimidin-2-yl)-aminocarbonyl]-2-(trifluoromethoxy)-benzenesulfonamide; and 2-Chloro-N—[(4,6-dimethylpyrimidin-2-yl)- | 40% |

| -continued | |
|---|---|
| Wettable Powder | |
| aminocarbonyl]-5-(trifluoromethoxy)-benzenesulfonamide | |
| sodium ligninsulfonate | 1.5% |
| low-viscosity methyl cellulose | 3% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

UTILITY

The compounds of Formula I are useful as herbicides. They may be applied either pre- or postemergence for the control of undesired vegetation in noncrop areas or for selective weed control in certain crops, e.g. wheat. Some of these compounds are useful for the pre- and/or postemergence control of nutsedge. By properly selecting rate and time of application, compounds of this invention may be used to modify plant growth beneficially.

The precise amount of the compound of Formula (I) to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. The lower rates of the range will generally be selected for lighter soils, for selective weed control in crops, or in situations where maximum persistence is not necessary. Some of the compounds of Formula (I) can be used at very low rates for plant growth modification, but higher rates may also be useful, depending on factors such as the crop being treated, timing of treatment, etc.

The compounds of Formula (I) may be combined with other herbicides and are particularly useful in combination with 3-(3,4-dichlorophenyl)-1,1-dimethylurea, the triazines such as 2-chloro-4-(ethylamino)-6-(isopropylamino)-s-triazine, the uracils such as 5-bromo-3-sec-butyl-6-methyluracil, N-(phosphonomethyl)glycine, 3-cyclohexyl-1-methyl-6-dimethylamino-s-triazine-2,4-(1H,3H)-dione, N,N-dimethyl-2,2-diphenylacetamide, 2,4-dichlorophenoxyacetic acid (and closely related compounds), 4-chloro-2-butynyl-3-chlorophenylcarbamate (Carbyne ®), diisopropylthiolcarbamic acid, ester with 2,3-dichloroallyl alcohol (Avadex ®), diisopropylthiolcarbamic acid, S-(2,3,3-trichloroallyl) ester (Avadex ® BW), ethyl-N-benzoyl-N-(3,4-dichlorophenyl)-2-aminopropionate (Suffix ®), 1,2-dimethyl-3,5-diphenylpyrazolium methyl-sulfate (Avenge ®), methyl 2-[4-(2,4-dichlorophenoxy)-phenoxy]-propanoate (Hoelon ®), 4-amino-6-tertbutyl-3-(methylthio)-1,2,4-triazin-5(4H)-one (Lexone ®), 3-(3,4-dichlorophenyl)-1-methoxy-1-methylurea (Lorox ®), 3-isopropyl-1H-2,1,3-benzothiodiazin-(4)-3H-one 2,2-dioxide, $\alpha,\alpha,\alpha$-trifluoro-2,6-dinitro-N,N-dipropyl-p-toluidine, 1,1'-dimethyl-4,4'-bipyridinium ion, monosodium methanearsonate, 2-chloro-2',6'-diethyl-(methoxymethyl)acetanilide, and 1,1-dimethyl-3-($\alpha,\alpha,\alpha$-trifluoro-m-tolyl)urea (Cotoran ®).

The activity of these compounds was discovered in greenhouse tests. The tests are described below and the data resulting from them are shown below.

TEST PROCEDURE

Seeds of crabgrass (Digitaria sp.), barnyardgrass (*Echinochloa crusgalli*), wild oats (*Avena fatua*), *Cassia tora*, morningglory (Ipomoea sp.), cocklebur (Xanthium sp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifloiate leaf expanding, crabgrass with two leaves, barnyardgrass with two leaves, wild oats with one leaf, cassia with three leaves (including cotyledonary ones), morningglory with four leaves (including cotyledonary ones), cocklebur with four leaves (including cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for repsonse to treatment.

Ratings for compounds tested by this procedure are recorded in Table A.

0=no effect
10=maximum effect
C=chlorosis or necrosis
E=emergence inhibition
G=growth retardation
H=formative effects
U=unusual pigmentation

TABLE A

POSTEMERGENCE

| Compound | Rate kg/ha | BUSH-BEAN | COT-TON | MORN-ING-GLORY | COCK-LEBUR | CAS-SIA | NUT-SEDGE | CRAB-GRASS | BARN-YARD-GRASS | WILD OATS | WHEAT | CORN | SOY-BEAN | RICE | SORGHUM |
|---|---|---|---|---|---|---|---|---|---|---|---|---|---|---|---|
| Cl–phenyl(SO₂NHCNH)–pyrimidine(CH₃,CH₃)–OCF₃, mixture with | 2/5 | 9C | 9C | 10C | 9C | 8C | 9C | 2C,5G | 3C,9H | 1C,5G | 1C | 2C,8H | 4C,9G | 3C,8G | 2C,9G |
| Cl–phenyl(SO₂NHCNH)–pyrimidine(CH₃,CH₃)–OCF₃ | | | | | | | | | | | | | | | |
| phenyl(SO₂–NH–C(=O)–NH)–pyrimidine(CH₃,CH₃)–OCH₂CF₃ | 0.4 | 9C | 9C | 9C | 9C | 9C | 9G | 9C | 5C,9H | 2C,9G | 1C,9G | 5U,9G | 5C,9G | 5C,9G | 3U,9G |
| OCF₂CHF₂–phenyl(SO₂–NH–C(=O)–NH)–pyrimidine(OCH₃,CH₃) | 0.4 | 9D,9G, 6Y | 5C,9G | 10C | 9C | 9C | 5G | 0 | 2G | 0 | 0 | 3G | 5C,9G | — | 3G |
| OCF₂CHF₂–phenyl(SO₂–NH–C(=O)–NH)–pyrimidine(OCH₃,OCH₃) | 0.4 | 9D,9G, 6Y | 6C,9G | 9C | 5C,9G | 9C | 1C | 1C,2H | 0 | 1C | 2C,9G | — | 1C,7G |

TABLE A-continued

| Compound | 0.4 | | | | | | | | | | | | | | | |
|---|---|---|---|---|---|---|---|---|---|---|---|---|---|---|---|---|
| 2-OCF$_2$CHF$_2$-phenyl-SO$_2$-NH-C(O)-NH-(4,6-dimethylpyrimidin-2-yl) | 0.4 | 9C | 6C,9G | 10C | 3C,8G | 1C,9G | 1C | 1C,4G | 1C | 1C | 7H | 2C,9G | — | 2C,9H |
| 2-OCF$_2$CHFCl-4-Cl-phenyl-SO$_2$-NH-C(O)-NH-(4,6-dimethylpyrimidin-2-yl) and/or | 0.4 | 3C,8G, 6Y | 3C,8G, 3C,9G | 3C,9G | 0 | 0 | 0 | 0 | 0 | 0 | 0 | 2C,2H, 5G | 0 | |
| 2-Cl-4-OCF$_2$CHFCl-phenyl-SO$_2$-NH-C(O)-NH-(4,6-dimethylpyrimidin-2-yl) | | | 9C | 10C | 1C | 1C,6G | 4G | 2G | 3G | 1C | 1C,3G | 1C,8G | 1C,5G | 1C,4G |
| 2-Br-4-OCF$_2$CHF$_2$-phenyl-SO$_2$-NH-C(O)-NH-(4,6-dimethylpyrimidin-2-yl) mixture with 2-OCF$_2$CHF$_2$-4-Br-phenyl-SO$_2$-NH-C(O)-NH-(4,6-dimethylpyrimidin-2-yl) | 0.4 | 3C,8G, 6Y | 3C,4H, 9G | 10C | 1C | 1C,6G | 4G | 2G | 3G | 1C | 1C,3G | 1C,8G | 1C,5G | 1C,4G |

TABLE A-continued

| Structure | | | | | | | | | | | | | |
|---|---|---|---|---|---|---|---|---|---|---|---|---|---|
| ![structure 1] mixture with OCF₂CHF₂ | 0.4 | 3C,7G, 6Y | 4C,9G | 9C | 2C | 1C | 2G | 1C | 0 | 3G | 2C,8G | 3G | 2G |
| ![structure 2] | 0.4 | 2C,4G | 2C,2H | 2C,8G | 2C,8G | 1C | 0 | 0 | 0 | 0 | 0 | 0 | 0 |
| ![structure 3] mixture with OCF₂CHFBr | 0.4 | 6C,9G | 5C,9G | 9C | 2C,6H | 8G | 1C,5G | 1C,5H | 5G | 3G | 9C | 6G | 1H,6G |

TABLE A-continued

| Structure | Rate kg/ha | MORNING-GLORY | COCK-LEBUR | CASSIA | NUT-SEDGE | CRAB-GRASS | BARNYARD-GRASS | WILD OATS | WHEAT | CORN | SOY-BEAN | RICE | SORGHUM |
|---|---|---|---|---|---|---|---|---|---|---|---|---|---|
| 2-SCF$_2$CHFCl-C$_6$H$_4$-SO$_2$-NH-C(=O)-NH-(4,6-dimethylpyrimidin-2-yl) | 0.4 | 4C,9G,6Y | 3C,4H | 2C,5G | 3C,5G | 1C,3G | 4G | 2G | 1C,5G | 0 | 0 | 2G | 1C,3G,3G | 1C,3G |
| 2-OCF$_2$CHFCF$_3$-C$_6$H$_4$-SO$_2$-NH-C(=O)-NH-(4-OCH$_3$-6-CH$_3$-pyrimidin-2-yl) | 0.4 | 10G,5C | 8G,3H,5C | 10C | 10C | 3G | 0 | 0 | 0 | 0 | 0 | 0 | 10G,7C | 0 | 0 |
| 2-OCF$_2$CHFCF$_3$-C$_6$H$_4$-SO$_2$-NH-C(=O)-NH-(4,6-dimethylpyrimidin-2-yl) | 0.4 | 4G,2C | 0 | 10G,7C | 7G,5H | 0 | 0 | 0 | 0 | 0 | 0 | 0 | 0 | 0 |
| 2-OCF$_2$CHFCF$_3$-C$_6$H$_4$-SO$_2$-NH-C(=O)-NH-(4,6-di-OCH$_3$-pyrimidin-2-yl) | 0.4 | 10G,3H,4C | 6G,3H,3C | 10C | 3C | 2C | 0 | 0 | 0 | 0 | 0 | 0 | 10G,6C | 0 | 0 |
| 2-OCF$_2$CHFCF$_3$-C$_6$H$_4$-SO$_2$-NH-C(=O)-NH-(4-OCH$_3$-6-CH$_3$-pyrimidin-2-yl) | 0.4 | 10G,7C | 7G,3H,3C | 10C | 3C | 3G | 0 | 0 | 0 | 0 | 0 | 0 | 10G,5C | 0 | 0 |

PRE-EMERGENCE

TABLE A-continued

| Structure | | | | | | | | | | | | | | |
|---|---|---|---|---|---|---|---|---|---|---|---|---|---|---|
| Cl-phenyl(SO₂NHC(O)NH)-pyrimidine(CH₃,CH₃) with OCF₃, mixture with Cl-phenyl(SO₂NHC(O)NH)-pyrimidine(CH₃,CH₃) OCF₃ | 2/5 | 9G | 9G | 9H | 2C 9G | 10E | 4G | 3C 9H | 2C 8G | 8G | 1U 9G | 9H | 9H | 2C 9H |
| phenyl(OCH₂CF₃)(SO₂NHC(O)NH)-pyrimidine(CH₃,CH₃) | 0.4 | 9G | 9H | 9G | 10E | 3C,9G | 9H | 2C,9H | 9H | 9G | 10E | 5C,9H |
| phenyl(OCF₂CHF₂)(SO₂NHC(O)NH)-pyrimidine(OCH₃,CH₃) | 0.4 | 9G | 9G | 5C,9G | 0 | 2G | 2C | 0 | 0 | 1C,6G | 9H | 1C,7G | 6G |
| phenyl(OCF₂CHF₂)(SO₂NHC(O)NH)-pyrimidine(OCH₃,OCH₃) | 0.4 | 9G | 9G | 9G | 10E | 2G | 2C,8H | 0 | 0 | 1C,7G | 9H | 8G | 9H |

TABLE A-continued

| Structure | | | | | | | | | | | | | | |
|---|---|---|---|---|---|---|---|---|---|---|---|---|---|---|
| OCF$_2$CHF$_2$-phenyl-SO$_2$-NH-C(=O)-NH-pyrimidine(CH$_3$,CH$_3$) | 0.4 | 8G | 9G | 9G | 10E | 0 | 2C,8H | 9G | 2G | 9H | 9H | 9H | 9H |  |
| OCF$_2$CHFCl-phenyl(Cl)-SO$_2$-NH-C(=O)-NH-pyrimidine(CH$_3$,CH$_3$) and/or Cl-phenyl(OCF$_2$CHFCl)-SO$_2$-NH-C(=O)-NH-pyrimidine(CH$_3$,CH$_3$) | 0.4 | 1C,7G | 8H | 1C | 0 | 0 | 4C | 0 | 0 | 1C,5G | 2H | 0 | 0 |  |
| Br-phenyl(OCF$_2$CHF$_2$)-SO$_2$-NH-C(=O)-NH-pyrimidine(CH$_3$,CH$_3$) mixture with OCF$_2$CHF$_2$-phenyl(Br)-SO$_2$-NH-C(=O)-NH-pyrimidine(CH$_3$,CH$_3$) | 0.4 | 1C,7G | 9G | 8G | 3G | 0 | 0 | 0 | 0 | 1C,6G | 1C,4G | 2G | 1C,3G |  |

TABLE A-continued

| Structure | | | | | | | | | | | | |
|---|---|---|---|---|---|---|---|---|---|---|---|---|
| Structure 1 (Cl, SO₂-NH-C(O)-NH-pyrimidine-CH₃,CH₃, OCF₂CHF₂) mixture with OCF₂CHF₂ isomer | 0.4 | 9G | 9G | 2G | 3G | 0 | 0 | 0 | 0 | 1C,6G | 1C | 1C,2G | 1C,5G |
| Structure 2 (OCF₂CHF₂, SO₂-NH-C(O)-NH-pyrimidine, Cl) | 0.4 | 7G | 7G | 0 | 0 | 0 | 0 | 0 | 0 | | | | |
| Structure 3 (Cl, SO₂-NH-C(O)-NH-pyrimidine, OCF₂CHFBr) mixture with OCF₂CHFBr isomer | | | | | | 1C | | 0 | 1C | 2G | 2C | 0 | |
| Structure 4 (OCF₂CHFBr, SO₂-NH-C(O)-NH-pyrimidine, Cl) | 0.4 | 8G | 8G | 10E | 10E | 1C,7G | 9H | 1C,7H | 1C,6G | 9G | 9H | 10E | 3C,9H |
| Structure 5 (CH₃, OCF₂CHF₂, SO₂-NH-C(O)-NH-pyrimidine, CH₃) | | | | | | | | | | | | | |

TABLE A-continued

| Structure | 0.4 | 7G | 10E | 8G | 10E | 3G | 1C,4G | 2G | 2G | 1C,5G | 1H | 9H | 1C,6G |
|---|---|---|---|---|---|---|---|---|---|---|---|---|---|
| Pyrimidine (CH₃, CH₃) — SO₂—NH—C(=O)—NH — SCF₂CHFCl | 0.4 | 8G,9C | 7G,7C | 0 | 0 | 0 | 0 | 0 | 0 | 0 | 0 | 0 | |
| Pyrimidine (OCH₃, CH₃) — SO₂—NH—C(=O)—NH — OCF₂CHFCF₃ | 0.4 | 0 | 8G,9C | 0 | 0 | 0 | 0 | 0 | 0 | 7G,5H | 0 | 0 | |
| Pyrimidine (CH₃, CH₃) — SO₂—NH—C(=O)—NH — OCF₂CHFCF₃ | 0.4 | 4G | 5G,5H | 5G | 3G | 4G | 3G | 0 | 0 | 0 | 0 | 4G,2H | |
| Pyrimidine (OCH₃, OCH₃) — SO₂—NH—C(=O)—NH — OCF₂CHFCF₃ | 0.4 | 8G | 6G,5H | 7G | 8G | 0 | 3G | 0 | 0 | 0 | 1C | 3C | 4G |
| Pyrimidine (OCH₃, CH₃) — SO₂—NH—C(=O)—NH — OCF₂CHFCF₃ | 0.4 | | | | | | | | 3G | 4G,3H | 4G,3H | 3C | 4G,3H |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated preemergence with test compounds within the scope of this invention.

Twenty-eight days after treatment, the plants were evaluated and visually rated for response to the chemical treatments utilizing the rating system described for test A. The data are summarized in Table B. Note that certain compounds are useful as preemergence treatments for weed control in wheat.

TABLE B

PRE-EMERGENCE ON FALLSINGTON SILT LOAM

| Compound | Rate kg/ha | Crabgrass | Barnyard-grass | Sorghum | Wild Oats | Johnson-grass | Dallis-grass | Giant Foxtail | Ky. Bluegrass | Cheatgrass | Corn | Mustard | Cockle-bur |
|---|---|---|---|---|---|---|---|---|---|---|---|---|---|
| ![structure 1: Cl, SO2NHCNH, pyrimidine(CH3,CH3), OCF3] | 1/16 | 4G | 6G | 7G 3H | 4G | 6G | 7G | 5G | 7G 5C | 7G | 8G 5H | 8G 9C | 8G 5C |
| | 1/4 | 4G | 8G 4C | 10C | 6G 3C | 8G 5C | 7G | 10C | 9G 9C | 9C | 8G 5H | 9G 9C | 9G 8C |
| mixture with | | | | | | | | | | | | | |
| ![structure 2: Cl, SO2NHCNH, pyrimidine(CH3,CH3), OCF3] | 0.06 | 0 | 0 | 6G,3H | 4G | 6G,3H | 3G | 3G | 5G | 5G | 3G | | — |
| | 0.25 | 0 | 2C | 9G,9C | 6G | 8G,3H | 5G | 6G | 7G,4C | 7G | 8G,3H | 10C | 7G |
| ![structure 3: SO2-NH-C(O)-NH, pyrimidine(CH3,CH3), OCF2CHF2] | 0.03 | 5G | 8G,5H | 10C | 6G | 7G,5H | 9G,5H | 4G | 7G | 5G,4C | 5G,3H | 9G,9C | 5G |
| | 0.12 | 7G,3H | 8G,5H | 10E | 6G | 8G,8H | 9G,5H | 7G,10H | 7G,3C | 7G,3H | 8G,7H | 10C | 5G,2H |
| ![structure 4: SO2-NH-C(O)-NH, pyrimidine(CH3,CH3), OCH2CF3] | | | | | | | | | | | | | |

TABLE B-continued
PRE-EMERGENCE ON FALLSINGTON SILT LOAM

| | Rate kg/ha | Pigweed | Nutsedge | Morningglory | Cassia | Teaweed | Velvetleaf | Jimsonweed | Soybean | Rice | Wheat | Sugarbeets | Cotton |
|---|---|---|---|---|---|---|---|---|---|---|---|---|---|
| | 0.06 | 0 | 0 | 5G,3H | 3G | 5G,3H | 0 | 3G | 0 | 2G | 0 | 8G,3C | 0 |
| | 0.25 | 0 | 0 | | | | | | 4G,2C | 5G,3C | 0 | 8G,8C | 3H |

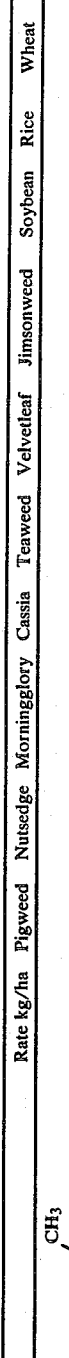

mixture with

| | Rate kg/ha | Pigweed | Nutsedge | Morningglory | Cassia | Teaweed | Velvetleaf | Jimsonweed | Soybean | Rice | Wheat | Sugarbeets | Cotton |
|---|---|---|---|---|---|---|---|---|---|---|---|---|---|
| | 1/16 | — | 10E | 8G | 7G | 10C | 9G 8C | 4G | 7G 5H | 6G | 0 | 7G | 7G 5H |
| | 1/4 | — | 10E | 8G | 7G | 10C | 10C | 5G 3C | 8G 5H | 8G 5C | 2G | 8G 5C | 8G |

| | Rate kg/ha | Pigweed | Nutsedge | Morningglory | Cassia | Teaweed | Velvetleaf | Jimsonweed | Soybean | Rice | Wheat | Sugarbeets | Cotton |
|---|---|---|---|---|---|---|---|---|---|---|---|---|---|
| | 0.06 | — | 8G | 4G | 5G | — | 10C | 0 | 6G,5H | 6G,7C | 5G,2C | 7G | 3G |
| | 0.25 | — | 10E | 8G | 7G,5C | — | 10C | 0 | 6G,5H | 5G,5C | 4G,2C | 10C | 6G,2H |

| | Rate kg/ha | Pigweed | Nutsedge | Morningglory | Cassia | Teaweed | Velvetleaf | Jimsonweed | Soybean | Rice | Wheat | Sugarbeets | Cotton |
|---|---|---|---|---|---|---|---|---|---|---|---|---|---|
| | 0.03 | — | 7G | 5G | 8G,6C | 4G | 7G,5C | 5G,3C | 7G,5H | 7G,5H | 5G | 7G,3H | 7G,5H |
| | 0.12 | — | 8G | 7G | 8G,6C | 6G,5C | 10C | 6G,5C | 7G,5H | 10C | 5G,2C | 7G,5H | 8G |

TABLE B-continued
PRE-EMERGENCE ON FALLSINGTON SILT LOAM

| Structure | Rate | | | | | | | | | | |
|---|---|---|---|---|---|---|---|---|---|---|---|
| ![structure: 2,6-disubstituted phenyl SO2-NH-C(=O)-NH-pyrimidine with 4,6-diCH3; phenyl substituents CH3 and OCF2CHF2] | 0.06<br>0.25 | 7G<br>10E | 0<br>0 | 0<br>6G | 0<br>2G | 0<br>3G | 0<br>0 | 5G<br>6G | 0<br>3G | 4G<br>5G | 0<br>2G |

TEST C

Purple nutsedge (*Cyperus rotundus*) tubers were planted about 2 cm deep in Fallsington silt loam soil contained in 10 cm diameter plastic pots. Five tubers were planted in each pot. Compounds of this invention were dissolved in a non-phytotoxic diluent and sprayed at 560 l/ha in four methods of application: soil surface, tuber/soil, soil incorporated, and postemergence. The soil surface spray consisted of spraying the compound on the surface of the firmed covering soil. The tuber/-soil spray consisted of spraying the compound on exposed tubers and subtending soil before adding the untreated covering soil. Soil incorporated treatment consisted of mixing the compound with the covering soil before using it to cover the tubers. The postemergence treatment was sprayed on nutsedge foliage and the surrounding soil surface when nutsedge had emerged and grown to a height of about 12 cm. Pots receiving the postemergence treatment were placed directly in the greenhouse. Pots receiving the other treatments were misted with about 0.3 cm water before being transferred to the greenhouse. Response ratings assessed after four weeks are recorded in Table C based on the same rating system as described in procedure A.

TABLE C

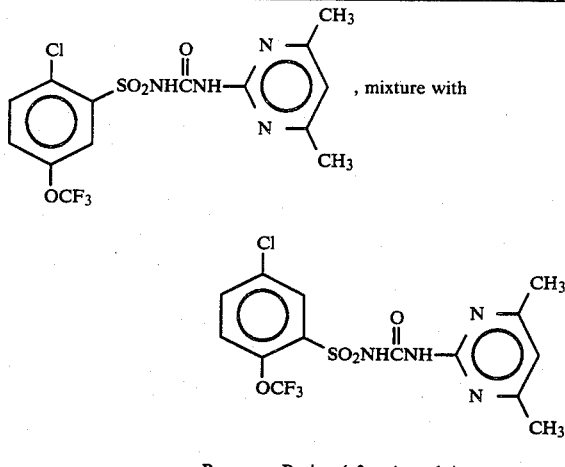

, mixture with

| Rate kg/ha | Response Rating (after 4 weeks) | | | |
|---|---|---|---|---|
| | Preemergence Soil Surface | Tuber Spray | Soil Incorporation | Post-emergence |
| .008 | 5G | 5G | 6G | 5G |
| .031 | 8G | 8G | 9G | 5C 9G |
| .125 | 10E | 8E 9G | 10E | 6C 9G |

TEST D

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*) and wild oats (*Avena fatua*). Approximately two weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table D. Several of the compounds tested by this procedure are useful for the post-emergence control of weeds in wheat, corn and rice.

TABLE D

| Structure | Rate kg/ha | Soy-beans | Vel-vet-leaf | Ses-ban-ia | Cas-sia | Cot-ton | Morn-ing-glory | Al-fal-fa | Jim-son-weed | Cock-le-bur | Corn | Crab-grass | Rice | Nut-sedge | Barn-yard-grass | Wheat | Giant Fox-tail | Wild Oats | Sor-ghum |
|---|---|---|---|---|---|---|---|---|---|---|---|---|---|---|---|---|---|---|---|
|  mixture with | 0.25 | 10G,8C | 10C | 10G,8C | 9G,4C | 8G,4C | 10G,7C | 8G,5C | 3G | 10C | 7G,3H | 0 | 6G,2C | 10G,5C | 4G,2C | 0 | 0 | 6G | 9G,5H |
| | 0.06 | 10G,8G | 10C | 8G,4C | 7G,3C | 8G,4C | 7G | 8G,4C | 0 | 10G,8C | 5G,3H | 0 | 6G | 10G,3C | 0 | 0 | 0 | 3G | 8G,5H |
| 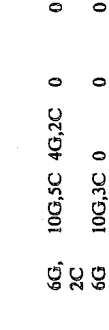 | 0.25 | 10G,6C | 9C | 10G,8C | 10G,8C | 10G,7C | 10C | 8C | — | 10C | 1G,1H | 2G | 2G,1C | 5G | 3G,1C | 0 | 0 | 1G | 1G |
| | 0.06 | 10G,6C | 9C | 10G,8C | 10G,6C | 10G,3C | 10C | 7C | — | 10C | 1G,2H | 0 | 1C | 6G | 3G,1C | 0 | 0 | 0 | 0 |
|  | 0.25 | 10G,7C | 9G,6C | 9C | 10G,7C | 10G,6C | 10G,8C | 7C | — | 10G,8C | 1G,1H | 1G | 1G | 9G,1C | 3G,1C | 0 | — | 1G | 4G,2C |
| | 0.06 | 10G,5C | 6G,2C | 10G,8C | 10G,6C | 10G,3C | 10G,9C | 4C | — | 10G,7C | 0 | 1G | 0 | 8G,2C | 4G,1C | 0 | — | 0 | 5G,3C |
|  | 0.25 | 10G,7C | 9G,8C | 10G,7C | 10G,7C | 10G,6C | 10G,8C | 5G,3C | 4G,3C | 10G,7C | 5G,3C | 3G,1C | 8G,2C | 8G,1C | 2G,1C | 5G | 5G,2C | 1G | 6G,2C |
| 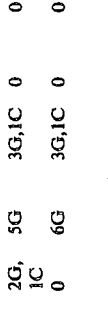 | 0.063 | 10G,6C | 10G,8C | 10G,8C | 10G,6C | 10G,3C | 10G,6C | 5G,3C | 0 | 9G,4C | 2G,1C | 0 | 6G,1C | 5G | 2G,1C | 2G | 4G | 7G,1C,4G | 4G,1C |

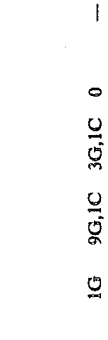

TABLE D-continued

| Structure | Rate kg/ha | Soy-beans | Vel-vet-leaf | Ses-ban-ia | Cas-sia | Cot-ton | Morn-ing-glory | Al-fal-fa | Jim-son-weed | Cock-le-bur | Corn | Crab-grass | Rice | Nut-sedge | Barn-yard-grass | Wheat | Giant Fox-tail | Wild Oats | Sor-ghum |
|---|---|---|---|---|---|---|---|---|---|---|---|---|---|---|---|---|---|---|---|
| 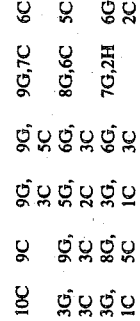 | 0.25 | 9G,3C | 10C | 9C | 9G,3C | 9G,5C | 9G,7C | 6C | — | 10G,8C | 2G | 2G | 9G,3C | 9G | 4G,1C | 1G | 0 | 4G | 9G,3C |
|  | 0.06 | 8G,2C | 3G,3C | 9G,3C | 5G,2C | 6G,3C | 8G,6C | 5C | — | 9G,9C | 2G | 0 | 6G,1C | 9G | 3G,1C | 1G | 0 | 3G | 9G,3C |
|  | 0.07 | 10G,6C | 3G,3C | 8G,5C | 3G,1C | 6G,3C | 7G,2H | 6G,2C | — | 7G,2C | 0 | 2G,1C | 3G | 6G | 2G | 0 | 3G | 0 | 5G,2C |
|  | 0.015 | 9G,4C | 3G,1C | 8G,3C | 1G,1C | 6G,2C | 7G | 2G,2C | 4G | 6G,1C | 0 | 0 | 2G | 7G | 1G | 0 | 2G | 0 | 4G |
| 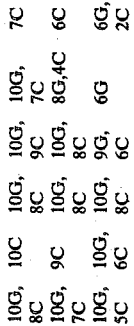 | 0.125 | 10G,7C | 10G,8C | 10C | 10G,8C | 10G,9C | 10G,7C | 7C | 9G,4C | 10G,9C | 9G,3C | 8G | 8G,3C | 10G | 10G,6C | 9G,3C | — | 7G | 9G,4C |
|  | 0.031 | 10G,7C | 10G,7C | 9C | 10G,8C | 9G,8C | 10G,8C | 6C | 9G,6C,3C | 9G,5C | 9G,3C | 7G | 8G,2C | 9G,2C | 10G,6C | 7G,2C | — | 7G,2C | 9G,2C |
|  | 0.008 | 10G,7C | 10G,5C | 10G,6C | 10G,8C | 9G,6C | 6G | 6G,2C | 6G,3C,2C | 9G,3C | 4H,5H | 2G | 8G,2C | 8G,4C | 8G,2C | 2G | 6G,1C | 7G,2C | 10G,4C |
| 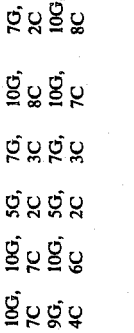 | 0.5 | 10G,5C | 10G,8C | 10G,7C | 5G,2C | 7G,3C | 10G,8C | 7G,2C | 9G,6C | 10G,8C | 0 | 0 | 4G | 6G | 1G | 0 | 0 | 0 | 1G |
|  | 0.125 | 10G,5C | 7C | 9C | 5G,3C | 7G,3C | 10G,8C | 10G,3C | 9G,6C,5C | 10G,8C | 0 | 1G | 2G | 6G | 1G | 0 | 0 | 0 | 1G |
| 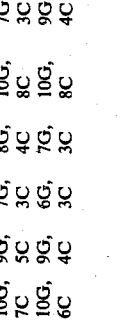 | 0.5 |  | 10G,6C | 10G,6C | 7G,3C | 8G,4C | 10G,8C | 10C | 7G,2C,7G | 10G,7C | 1G | 0 | 3G,1C,3G,1C | 8G,2C | 1G | 0 | 0 | 0 | 1G |
|  | 0.125 |  | 10G,6C | 9G,3C | 6G,3C | 7G,3C | 10G,8C | 10C | | 9G,6C | 0 | 1G | 2G | 7G,1C | 0 | 0 | 0 | 0 | 1G |
| 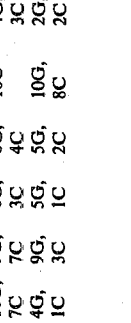 | 0.5 | 10G,6C | 4G,1C | 9G,3C | 5G,2C | 5G,2C | 10C | 4G,3C,2C | 7G,3C,1C | 9G,5C | 1G | 2G | 5G,1C,7G,2C | 8G,1C,7G,1C | 2G | 0 | 3G,1C | 1G | 1G |
|  | 0.125 | 7G,3C | 1C | | | | | | | 9G,3C | 0 | 2G,1C | | | 0 | 0 | 1C | 0 | 1G |

TEST E

Fifteen and twenty-five cm diameter plastic pots filled with Fallsington silt loam were planted with corn (*Zea mays*), cocklebur (*Xanthium pennsylvanicum*), morningglory (*Ipomea hederacea*), field bindweed (*Convolulus arvensis*), smartweed (Polygonum spp.), jimsonweed (*Datura stramonium*), lambsquaters (*Chenopodium album*), cassia (*Cassia tora*), pigweed (*Amaranthus retroflexus*), johnsongrass (*Sorghum halepense*), barnyardgrass (*Echinochloa crusgalli*), giant foxtail (*Setaria faberii*), crabgrass (Digitaria spp.) and nutsedge (*Cyperus rotundus*). Varying from two to three weeks after planting, the young plants and the soil around them were sprayed overall with the test chemicals dissolved in a nonphytotoxic solvent. Two weeks after treatment, all species were compared to untreated controls and visually rated for response to treatment. The rating system was as described previously for Test A. The data are presented in Table E. The compounds tested by this procedure show possible usefulness for postemergence control of weeds in corn.

TABLE E

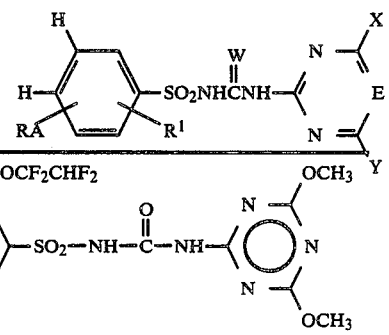

| Rate kg/ha | 1/32 | 1/3 | 1/32 | 1/8 |
|---|---|---|---|---|
| Corn | 0 | 2G,1C | 1G | 2G |
| Cocklebur | 10G,8C | 10G,9C | 10C | 10C |
| Morningglory | 10C | 10C | 10G,9C | 10G,9C |
| Field Bindweed | 8C | 10C | 8C | 10C |
| Smartweed | 10G,7C | 10G,8C | 10G,7C | 10G,9C |
| Jimsonweed | 9G,6C | 9G,6C | 6G | 8G,3C |
| Lambsquarter | 9G,5C | 10G,6C | 7G | 8G,3C |
| Cassia | 19G,7C | 10G,7C | 10G,7C | 10G,7C |
| Pigweed | 9G,3C | 10G,7C | 9G,3C | 10G,8C |
| Johnnsongrass | 3G | — | 2G,1U | 7G,3U |
| Barnyardgrass | 0 | 1G | 1G | 2G,1C |
| Giant Foxtail | 0 | 0 | 3G | 4G |
| Crabgrass | 0 | 0 | 1G | 2G |
| Nutsedge | 0 | 0 | 7G,2C | 8G,3C |

TEST F

The following table, Table F, is presented to additionally illustrate the biological activity of the compounds of the present invention. The data illustrate the efficacy of the compounds for the control of weeds in rice cultures.

Rice plants 10.5 cm tall were transplanted into paddies containing soil, sprouting barnyardgrass (*Echinochloa crusgalli*), seeds, sprouting water chestnut (*Eleocharis* spp.) tubers, arrowhead (*Sagittaria latifolia*) tubers, and *Scirpus mucronatus* seeds. The test compound was applied directly into the water, which was maintained at a few centimeters above the soil surface. Ratings (same system as in Table A) were taken on rice four days after application; ratings were taken for all species including rice four weeks after application.

TABLE F

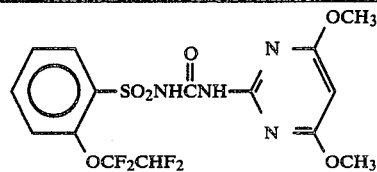

| Rate kg/ha | Rice 4 days | Rice 4 wks | Barnyardgrass 4 weeks | Water Chestnut 4 weeks | Arrowhead 4 weeks | *Scirpus mucronatus* 4 weeks |
|---|---|---|---|---|---|---|
| 25 | 0 | 0 | 2G | 10G | 10E | 10C |
| 100 | 0 | 0 | 7G | 10G,5C | 10E | 10C |

What is claimed is:

1. A compound selected from wherein
W is O or S;
R is $CHF_2$, $CF_3$, $CH_2CF_3$ or $CF_2CHFG$, where G is F, Cl, $CF_3$ or Br;
A is O or $S(O)_n$, where n is 0, 1 or 2;
$R^1$ is H, F, Cl, Br or $CH_3$;
X is $CH_3$ or $OCH_3$;
Y is $CH_3$, $OCH_3$, $OCH_2CH_3$, $(CH_2)_mOCH_3$ (where m is 1 or 2), $OCH_2CH_2OCH_3$, or $OCHR^2CO_2R^3$, where $R^2$ is H or $CH_3$ and $R^3$ is $CH_3$ or $C_2H_5$; and
E is CH and agriculturally suitable salts thereof.
2. A compound of claim 1 wherein W is O.
3. A compound of claim 2 wherein Y is $CH_3$ or $CH_3O$.
4. A compound of claim 3 wherein A is O, S or $SO_2$.
5. A compound of claim 3 wherein $R^1$ is H or Cl.
6. A compound of claim 3 wherein $R^1$ is H or Cl.

7. The compound of claim 1, 5-chloro-N-[(4,6-dimethylpyrimidin-2-yl)aminocarbonyl]-2-(trifluoromethoxy)benzenesulfonamide.

8. The compound of claim 1, 2-chloro-N-[(4,6-dimethylpyrimidin-2-yl)aminocarbonyl]-5-(trifluoromethoxy)benzenesulfonamide.

9. The compound of claim 1, N-[(4,6-dimethylpyrimidin-2-yl)aminocarbonyl]-2-(1,1,2,2-tetrafluoroethoxy)benzenesulfonamide.

10. The compound of claim 1, N-[(4,6-dimethoxypyrimidin-2-yl)aminocarbonyl]-2-(1,1,2,2-tetrafluoroethoxy)benzenesulfonamide.

11. The compound of claim 1, N-[(4-methoxy-6-methylpyrimidin-2-yl)aminocarbonyl]-2-(1,1,2,2-tetrafluoroethoxy)benzenesulfonamide.

12. A mixture of a compound of claim 1 consisting essentially of 5-chloro-N-[(4,6-dimethylpyrimidin-2-yl)aminocarbonyl]-2-(trifluoromethoxy)benzenesulfonamide, and 2-chloro-N-[(4,6-dimethylpyrimidin-2-yl)-aminocarbonyl]-5-(trifluoromethoxy)benzenesulfonamide.

13. A composition for the control of undesirable vegetation consisting essentially of a compound of claim 1 and at least one of (a) a surface-active agent and (b) a solid or liquid diluent.

14. A composition for the control of undesirable vegetation consisting essentially of a compound of claim 2 and at least one of (a) a surface-active agent and (b) a solid or liquid diluent.

15. A composition for the control of undesirable vegetation consisting essentially of a compound of claim 3 and at least one of (a) a surface-active agent and (b) a solid or liquid diluent.

16. A composition for the control of undesirable vegetation consisting essentially of a compound of claim 4 and at least one of (a) a surface-active agent and (b) a solid or liquid diluent.

17. A composition for the control of undesirable vegetation consisting essentially of a compound of claim 5 and at least one of (a) a surface-active agent and (b) a solid or liquid diluent.

18. A composition for the control of undesirable vegetation consisting essentially of the compounds of claim 12 and at least one of (a) a surface-active agent and (b) a solid or liquid diluent.

19. A method for control of undesirable vegetation comprising applying to the locus of such undesirable vegetation a herbicidally effective amount of a compound of claim 1.

20. A method for control of undesirable vegetation comprising applying to the locus of such undesirable vegetation a herbicidally effective amount of a compound of claim 2.

21. A method for the control of undesirable vegetation comprising applying to the locus of such undesirable vegetation a herbicidally effective amount of a compound of claim 3.

22. A method for the control of undesirable vegetation comprising applying to the locus of such undesirable vegetation a herbicidally effective amount of a compound of claim 4.

23. A method for the control of undesirable vegetation comprising applying to the locus of such undesirable vegetation a herbicidally effective amount of a compound of claim 5.

24. A method for the control of undesirable vegetation comprising applying to the locus of such undesirable vegetation herbicidally effective amount of the compounds of claim 6.

* * * * *